US010653767B2

(12) United States Patent
Ciaramella et al.

(10) Patent No.: US 10,653,767 B2
(45) Date of Patent: May 19, 2020

(54) ZIKA VIRUS MRNA VACCINES

(71) Applicant: ModernaTX, Inc., Cambridge, MA (US)

(72) Inventors: Giuseppe Ciaramella, Sudbury, MA (US); Sunny Himansu, Winchester, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/131,793

(22) Filed: Sep. 14, 2018

(65) Prior Publication Data

US 2019/0099481 A1    Apr. 4, 2019

Related U.S. Application Data

(60) Provisional application No. 62/558,746, filed on Sep. 14, 2017.

(51) Int. Cl.
*A61K 39/12* (2006.01)
*A61P 31/14* (2006.01)
*A61K 39/00* (2006.01)

(52) U.S. Cl.
CPC ............. *A61K 39/12* (2013.01); *A61P 31/14* (2018.01); *A61K 2039/53* (2013.01); *A61K 2039/54* (2013.01); *A61K 2039/545* (2013.01); *A61K 2039/575* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 3,906,092 A | 9/1975 | Hilleman et al. |
| 6,500,419 B1 | 12/2002 | Hone et al. |
| 6,514,948 B1 | 2/2003 | Raz et al. |
| 6,610,044 B2 | 8/2003 | Mathiesen |
| 7,001,890 B1 | 2/2006 | Wagner et al. |
| 8,217,016 B2 | 7/2012 | Hoerr et al. |
| 8,569,256 B2 | 10/2013 | Heyes et al. |
| 8,609,142 B2 | 12/2013 | Troiano et al. |
| 8,613,954 B2 | 12/2013 | Zale et al. |
| 8,617,608 B2 | 12/2013 | Zale et al. |
| 8,673,316 B2 | 3/2014 | Kinney et al. |
| 8,691,961 B1 | 4/2014 | Puffer et al. |
| 8,710,200 B2 | 4/2014 | Schrum et al. |
| 8,734,832 B2 | 5/2014 | O'Hagan et al. |
| 8,734,853 B2 | 5/2014 | Sood et al. |
| 8,754,062 B2 | 6/2014 | de Fougerolles et al. |
| 8,822,663 B2 | 9/2014 | Schrum et al. |
| 8,999,380 B2 | 4/2015 | Bancel et al. |
| 9,000,141 B2 | 4/2015 | Chang et al. |
| 9,221,891 B2 | 12/2015 | Bancel et al. |
| 9,267,114 B2 | 2/2016 | Yamshchikov et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,597,380 B2 | 3/2017 | Chakraborty et al. |
| 9,868,691 B2 | 1/2018 | Benenato et al. |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,273,269 B2 | 4/2019 | Ciaramella |
| 2001/0001066 A1 | 5/2001 | Cezayirli et al. |
| 2003/0032615 A1 | 2/2003 | Felgner et al. |
| 2003/0092653 A1 | 5/2003 | Kisich et al. |
| 2005/0032730 A1 | 2/2005 | Von Der Mulbe et al. |
| 2005/0059624 A1 | 3/2005 | Hoerr et al. |
| 2005/0250723 A1 | 11/2005 | Hoerr et al. |
| 2006/0172003 A1 | 8/2006 | Meers et al. |
| 2006/0172966 A1 | 8/2006 | Lipford et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mulbe et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0250225 A1 | 10/2011 | Fotin-Mleczek et al. |
| 2011/0269950 A1 | 11/2011 | Von Der Mulbe et al. |
| 2011/0311472 A1 | 12/2011 | Hoerr et al. |
| 2012/0009221 A1 | 1/2012 | Hoerr et al. |
| 2012/0189700 A1 | 7/2012 | Aguilar et al. |
| 2012/0219573 A1 | 8/2012 | Baumhof et al. |
| 2012/0258046 A1 | 10/2012 | Mutske |
| 2013/0022538 A1 | 1/2013 | Rossi |

(Continued)

FOREIGN PATENT DOCUMENTS

AU    652831 B2    9/1994
CA    2473135    6/2003

(Continued)

OTHER PUBLICATIONS

U.S. Appl. No. 15/239,613, filed Aug. 17, 2016, Laska et al.
U.S. Appl. No. 16/036,318, filed Jul. 16, 2018, Ciaramella et al.
U.S. Appl. No. 16/048,154, filed Jul. 27, 2018, Ciaramella et al.
U.S. Appl. No. 16/144,394, filed Sep. 27, 2018, Ciaramella et al.
U.S. Appl. No. 90/014,167, filed Aug. 17, 2018, Ciaramella et al.
U.S. Appl. No. 15/748,773, filed Jan. 30, 2018, Ciaramella et al.
U.S. Appl. No. 15/155,986, filed May 16, 2016, Fritz.
U.S. Appl. No. 15/753,293, filed Feb. 17, 2018, Smith.

(Continued)

*Primary Examiner* — Benjamin P Blumel
(74) *Attorney, Agent, or Firm* — Wolf, Greenfield & Sacks, P.C.

(57) ABSTRACT

Provided herein, in some embodiments, are Zika virus RNA vaccines and methods of producing an antigen-specific immune response in a subject.

19 Claims, 2 Drawing Sheets
Specification includes a Sequence Listing.

(56) References Cited

U.S. PATENT DOCUMENTS

| | | |
|---|---|---|
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0156849 A1 | 6/2013 | de Fougerolles et al. |
| 2013/0171241 A1 | 7/2013 | Geall |
| 2013/0183355 A1 | 7/2013 | Jain et al. |
| 2013/0189351 A1 | 7/2013 | Geall |
| 2013/0195867 A1 | 8/2013 | Hoerr et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236533 A1 | 9/2013 | Von Andrian et al. |
| 2013/0243848 A1 | 9/2013 | Lobovkina et al. |
| 2013/0245103 A1 | 9/2013 | de Fougerolles et al. |
| 2013/0259923 A1 | 10/2013 | Bancel et al. |
| 2013/0266640 A1 | 10/2013 | De Fougerolles et al. |
| 2013/0295043 A1 | 11/2013 | Kallen et al. |
| 2013/0336998 A1 | 12/2013 | Kallen et al. |
| 2014/0037660 A1 | 2/2014 | Folin-Mleczek et al. |
| 2014/0065228 A1 | 3/2014 | Yarowoski et al. |
| 2014/0134201 A1 | 5/2014 | Tureci et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0271829 A1 | 9/2014 | Lilja et al. |
| 2014/0378538 A1 | 12/2014 | Bancel |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0271272 A1 | 9/2016 | Bancel et al. |
| 2016/0317647 A1 | 11/2016 | Ciaramella et al. |
| 2016/0331828 A1 | 11/2016 | Ciaramella et al. |
| 2016/0367658 A1 | 12/2016 | Kinney et al. |
| 2017/0065675 A1 | 3/2017 | Bancel et al. |
| 2017/0130255 A1 | 5/2017 | Wang et al. |
| 2017/0202979 A1 | 7/2017 | Chakraborty et al. |
| 2017/0340724 A1 | 11/2017 | Ciaramella et al. |
| 2017/0340725 A1 | 11/2017 | Ciaramella et al. |
| 2018/0000953 A1 | 1/2018 | Almarsson et al. |
| 2018/0002393 A1 | 1/2018 | Bancel et al. |
| 2018/0028645 A1 | 2/2018 | Ciaramella et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0312549 A1 | 11/2018 | Ciaramella |
| 2018/0318409 A1 | 11/2018 | Valiante et al. |
| 2018/0363019 A1 | 12/2018 | Hoge |
| 2019/0008938 A1 | 1/2019 | Ciaramella et al. |
| 2019/0099481 A1 | 4/2019 | Ciaramella et al. |
| 2019/0192646 A1 | 6/2019 | Cohen et al. |

FOREIGN PATENT DOCUMENTS

| | | |
|---|---|---|
| EP | 1026253 | 8/2000 |
| EP | 1083232 | 2/2005 |
| EP | 1301614 B1 | 11/2006 |
| EP | 1383556 B1 | 10/2007 |
| EP | 1905844 A2 | 2/2008 |
| EP | 2188379 B1 | 1/2013 |
| EP | 2548960 A1 | 1/2013 |
| WO | WO 1987/005326 A1 | 9/1987 |
| WO | WO 1990/011092 A1 | 10/1990 |
| WO | WO 1993/014778 A1 | 8/1993 |
| WO | WO 1995/024485 A2 | 9/1995 |
| WO | WO 1995/026204 A1 | 10/1995 |
| WO | WO 1995/033835 A1 | 12/1995 |
| WO | WO 1999/033982 A2 | 7/1999 |
| WO | WO 1999/052503 A2 | 10/1999 |
| WO | WO 2001/021810 A1 | 3/2001 |
| WO | WO 2004/058166 A2 | 7/2004 |
| WO | WO 2004/076645 A1 | 9/2004 |
| WO | WO 2005/007689 A1 | 1/2005 |
| WO | WO 2005/009346 | 2/2005 |
| WO | WO 2006/056027 A1 | 6/2006 |
| WO | WO 2006/071903 | 7/2006 |
| WO | WO 2006/095259 | 9/2006 |
| WO | WO 2007/095976 A2 | 8/2007 |
| WO | WO 2008/014979 A3 | 2/2008 |
| WO | WO 2008/052770 A2 | 5/2008 |
| WO | WO 2008/083949 A2 | 7/2008 |
| WO | WO 2009/030254 A1 | 3/2009 |
| WO | WO 2009/030481 A1 | 3/2009 |
| WO | WO 2009/095226 | 8/2009 |
| WO | WO 2009/127230 A1 | 10/2009 |
| WO | WO 2010/037408 A1 | 4/2010 |
| WO | WO 2010/037539 A1 | 4/2010 |
| WO | WO 2010/042877 A1 | 4/2010 |
| WO | WO 2010/054406 A1 | 5/2010 |
| WO | WO 2010/088927 A1 | 8/2010 |
| WO | WO 2010/115046 A2 | 10/2010 |
| WO | WO 2011/005799 A2 | 1/2011 |
| WO | WO 2011/026641 A9 | 3/2011 |
| WO | WO 2011/068810 A1 | 6/2011 |
| WO | WO 2011/069529 A1 | 6/2011 |
| WO | WO 2011/069586 A1 | 6/2011 |
| WO | WO 2011/144358 A1 | 11/2011 |
| WO | WO 2012/006369 A2 | 1/2012 |
| WO | WO 2012/006380 A2 | 1/2012 |
| WO | WO 2012/019630 A1 | 2/2012 |
| WO | WO 2012/019780 A1 | 2/2012 |
| WO | WO 2012/075040 A2 | 6/2012 |
| WO | WO 2012/089225 A1 | 7/2012 |
| WO | WO 2012/113513 A1 | 8/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A1 | 9/2012 |
| WO | WO 2013/006834 A1 | 1/2013 |
| WO | WO 2013/006837 A1 | 1/2013 |
| WO | WO 2013/006838 A1 | 1/2013 |
| WO | WO 2013/006842 A2 | 1/2013 |
| WO | WO 2013/030778 A2 | 3/2013 |
| WO | WO 2013/052167 A2 | 4/2013 |
| WO | WO 2013/055905 A1 | 4/2013 |
| WO | WO 2013/056132 A2 | 4/2013 |
| WO | WO 2013/059496 A1 | 4/2013 |
| WO | WO 2013/090186 A1 | 6/2013 |
| WO | WO 2013/102203 A1 | 7/2013 |
| WO | WO 2013/113502 A1 | 8/2013 |
| WO | WO 2013/120497 A1 | 8/2013 |
| WO | WO 2013/120628 A1 | 8/2013 |
| WO | WO 2013/120629 A1 | 8/2013 |
| WO | WO 2013/174409 A1 | 11/2013 |
| WO | WO 2013/185069 A1 | 12/2013 |
| WO | WO 2014/071963 A1 | 5/2014 |
| WO | WO 2014/072061 A1 | 5/2014 |
| WO | WO 2014/127917 A1 | 8/2014 |
| WO | WO 2014/144196 A1 | 9/2014 |
| WO | WO 2014/152774 A1 | 9/2014 |
| WO | WO 2014/152940 A1 | 9/2014 |
| WO | WO 2014/160243 A1 | 10/2014 |
| WO | WO 2015/013551 A1 | 1/2015 |
| WO | WO 2015/024667 A1 | 2/2015 |
| WO | WO 2015/024668 A2 | 2/2015 |
| WO | WO 2015/164674 A1 | 4/2015 |
| WO | WO 2015/130584 A1 | 9/2015 |
| WO | WO 2015/189425 A1 | 12/2015 |
| WO | WO 2016/044023 A1 | 3/2016 |
| WO | WO 2016/092460 A2 | 6/2016 |
| WO | WO 2016/116904 A1 | 7/2016 |

(56) References Cited

FOREIGN PATENT DOCUMENTS

| WO | WO 2016/164762 A1 | 10/2016 |
|----|----|----|
| WO | WO 2016/176330 A1 | 11/2016 |
| WO | WO 2016/184822 A1 | 11/2016 |
| WO | WO 2016/201377 A1 | 12/2016 |
| WO | WO 2016/203025 A1 | 12/2016 |
| WO | WO 2017/015457 A1 | 1/2017 |
| WO | WO 2017/015463 A1 | 1/2017 |
| WO | WO 2017/020026 A1 | 2/2017 |
| WO | WO 2017/021546 A1 | 2/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070624 A1 | 4/2017 |
| WO | WO 2017/109222 | 6/2017 |
| WO | WO 2017/140905 | 8/2017 |
| WO | WO 2017/147458 | 8/2017 |
| WO | WO 2017/162265 A1 | 9/2017 |
| WO | WO 2017/165317 A1 | 9/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/208191 A1 | 12/2017 |
| WO | WO 2017/210215 | 12/2017 |
| WO | WO 2017/210364 A1 | 12/2017 |
| WO | WO 2018/020271 A1 | 2/2018 |
| WO | WO 2018/052549 | 3/2018 |
| WO | WO 2018/053209 A1 | 3/2018 |
| WO | WO 2018/075980 A1 | 4/2018 |
| WO | WO 2018/081459 A1 | 5/2018 |
| WO | WO 2018/089851 A1 | 5/2018 |
| WO | WO 2018/091540 | 5/2018 |
| WO | WO 2018/107088 A1 | 6/2018 |
| WO | WO 2018/111967 A1 | 6/2018 |
| WO | WO 2018/132537 A1 | 7/2018 |
| WO | WO 2018/144082 A1 | 8/2018 |
| WO | WO 2018/144778 A1 | 8/2018 |
| WO | WO 2018/151816 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |

OTHER PUBLICATIONS

U.S. Appl. No. 15/753,297, filed Feb. 17, 2018, Thompson.
U.S. Appl. No. 15/748,782, filed Jan. 30, 2018, Mousavi et al.
U.S. Appl. No. 16/001,751, filed Jun. 6, 2018, Mousavi et al.
U.S. Appl. No. 15/156,249, filed May 16, 2016, Miracco.
U.S. Appl. No. 15/767,587, filed Apr. 11, 2018, Ciaramella.
U.S. Appl. No. 16/006,526, filed Jun. 12, 2018, Ciaramella.
U.S. Appl. No. 15/767,600, filed Apr. 11, 2018, Ciaramella et al.
U.S. Appl. No. 16/023,013, filed Jun. 29, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/136,386, filed Sep. 20, 2018, Ciaramella et al.
U.S. Appl. No. 15/674,591, filed Aug. 11, 2017, Ciaramella et al.
U.S. Appl. No. 16/136,503, filed Sep. 20, 2018, Ciaramella et al.
U.S. Appl. No. 15/746,286, filed Jan. 19, 2018, Ciaramella et al.
U.S. Appl. No. 16/009,811, filed Jun. 15, 2018, Ciaramella et al.
U.S. Appl. No. 16/009,848, filed Jun. 15, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 15/905,576, filed Feb. 26, 2018, Bancel et al.
U.S. Appl. No. 15/387,263, filed Dec. 21, 2016, Chen et al.
U.S. Appl. No. 15/674,107, filed Aug. 10, 2017, Besin et al.
U.S. Appl. No. 15/674,872, filed Aug. 11, 2017, Besin et al.
U.S. Appl. No. 16/001,786, filed Jun. 6, 2018, Hoge et al.
U.S. Appl. No. 16/040,981, filed Jul. 20, 2018, Ciaramella et al.
U.S. Appl. No. 16/001,765, filed Jun. 6, 2018, Marquardt et al.
U.S. Appl. No. 15/880,436, filed Jan. 25, 2018, Ciaramella.
U.S. Appl. No. 16/031,951, filed Jul. 10, 2018, Ciaramella.
U.S. Appl. No. 16/302,607, filed Nov. 16, 2018, Benenato et al.
U.S. Appl. No. 16/180,076, filed Nov. 5, 2018, Cohen et al.
Wong et al., An mRNA-based vaccine strategy against Zika. Cell Res. Sep. 2017;27(9):1077-1078. doi: 10.1038/cr.2017.53. Epub Apr. 11, 2017.
Chahal et al., An RNA nanoparticle vaccine against Zika Vims elicits antibody and CD8+ T cell responses in a mouse model. Sci Rep. Mar. 21, 2017;7(1):252. doi: 10.1038/s41598-017-00193-W.
Dowd et al., Rapid development of a DNA vaccine for Zika virus.Science. Oct. 14, 2016;354(6309):237-240. Epub Sep. 22, 2016.
[No Author Listed], "Messenger RNA", Internet: Wikipedia. Jun. 19, 2013, XP002699196, Retrieved from the Internet: URL: http://en.wikipedia.org/wiki/Messenger RNA.
Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.
Archer, Induction of a T-cell specific antigen on bone marrow lymphocytes with thymus RNA. Immunology. Jan. 1978;34(1):123-9.
Ashley et al., Bone marrow-generated dendritic cells pulsed with tumor extracts or tumor RNA induce antitumor immunity against central nervous system tumors. J Exp Med. Oct. 6, 1997; 186(7): 1177-82.
Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.
Bettinger et al., Peptide-mediated RNA delivery: a novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion. J Infect Dis. Mar. 15, 2015;211(6):947-55. doi: 10.1093/infdis/jiu522. Epub Sep. 18, 2014.
Bonehill et al., Single-step antigen loading and activation of dendritic cells by mRNA electroporation for the purpose of therapeutic vaccination in melanoma patients. Clin Cancer Res. May 2009; 15(10): 3366-3375.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Cheng et al., Multifunctional triblock copolymers for intracellular messenger RNA delivery. Biomaterials. Oct. 2012; 33(28): 6868-6876.
Conry et al., Characterization of a messenger RNA polynucleotide vaccine vector. Cancer Res. Apr. 1, 1995 ;55 (7):1397-1400.
Cu et al., Enhanced Delivery and Potency of Self-Amplifying mRNA Vaccines by Electroporation in Situ, Vaccines, 2013, 1, 367-383. Abstract Only.
Dahlman et al., In vivo endothelial siRNA delivery using polymeric nanoparticles with low molecular weight. Nat Nanotechnol. Aug. 2014;9(8):648-655. doi: 10.1038/nnano.2014.84. Epub May 11, 2014.
Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.

(56) References Cited

OTHER PUBLICATIONS

Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.

Garcia-Arriaza et al., A novel poxvirus-based vaccine, MVA-CHIKV, is highly immunogenic and protects mice against chikungunya infection. J Virol. Mar. 2014;88(6):3527-47. doi: 10.1128/Jvi.03418-13. Epub Jan. 8, 2014.

Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.

GenBank Accession No. KJ776791, first seen on NCBI on May 12, 2014.

Gilboa et al., Cancer immunotherapy with mRNA-transfected dendritic cells. Immunol Rev. Jun. 2004;199:251-63.

Gupta et al., ZikaVR: An Integrated Zika Virus Resource for Genomics, Proteomics, Phylogenetic and Therapeutic Analysis. Sci Rep. Sep. 16, 2016;6:32713. doi: 10.1038/srep32713.

Hecker et al., Non-Viral DNA and mRNA Gene Delivery to the CNS Pre-Operatively for Neuroprotection and Following Neurotrauma. Molecular Therapy. 2004; 9, S258-S258.

Heiser et al., Induction of polyclonal prostate cancer-specific CTL using dendritic cells transfected with amplified tumor RNA. J Immunol. Mar. 1, 2001; 166(5):2953-60.

Heyes et al., Cationic lipid saturation influences intracellular delivery of encapsulated nucleic acids. J Control Release. Oct. 3, 2005;107(2):276-87.

Hoerr et al., In vivo application of RNA leads to induction of specific cytotoxic T lymphocytes and antibodies. EurJ Immunol. Jan. 2000;30(1):1-7.

Hoerr et al., Stabilized Messenger RNA (RNActiveTM) as a Tool for Innovative Gene Delivery. Tissue Engineering. Apr. 2007; 13(4): 865-925.

Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].

Holtkamp et al., Modification of antigen-encoding RNA increases stability, translational efficacy, and T-cell stimulatory capacity of dendritic cells. Blood. Dec. 15, 2006;108(13):4009-17.

Jirikowski et al., Reversal of diabetes insipidus in Brattleboro Rats: Intrahypothalamic injection of vasopressin mRNA. Science. Feb. 1992; 255(5047): 996-998.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 213. Review.

Kanapathipillai et al., Nanoparticle targeting of anti-cancer drugs that alter intracellular signaling or influence the tumor microenvironment. Adv Drug Deliv Rev. Dec. 15, 2014;79-80:107-18. doi: 10.1016/j.addr.2014.05.005. Epub May 9, 2014.

Kariko et al., Generating the optimal mRNA for therapy: HPLC purification eliminates immune activation and improves translation of nucleoside-modified, protein-encoding mRNA, NucleicAcids Research, Oxford University Press, GB, vol. 39, No. 21, Sep. 2, 2011 (Sep. 2, 2011), e142. doi: 10.1093/nar/gkr695. Epub Sep. 2, 2011.

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kisich et al., Antimycobacterial agent based on mRNA encoding human beta-defensin 2 enables primary macrophages to restrict growth of Mycobacterium tuberculosis.Infect Immun Apr. 2001;69(4):2692-9.

Kozielski et al., Bioreducible Cationic Polymer-Based Nanoparticles for Efficient and Environmentally Triggered Cytoplasmic siRNA Delivery to Primary Human Brain Cancer Cells, ACS Nano. Apr. 22, 2014;8(4):3232-41. doi: 10.1021/nn500704t. Epub Apr. 3, 2014.

Kreiter et al., Intranodal vaccination with naked antigen-encoding RNA elicits potent prophylactic and therapeutic antitumoral immunity. Cancer Res. 2010; 70: 9031-9040.

Kreiter et al., Tumor vaccination using messenger RNA: prospects of a future therapy. Curr Opinion in Immun. Jun. 2011; 23(3): 399-406.

Kuhn et al., mRNA as a versatile tool for exogenous protein expression. Current Gene Therapy. Oct. 2012; 12 (5): 347-361.

Leitner et al., DNA and RNA-based vaccines: principles, progress and prospects. Vaccine. Dec. 10, 1999;18 (9-10):765-77.

Li et al., Overcoming obstacles to develop effective and safe siRNA therapeutics. Expert Opin Biol Ther. May 2009; 9(5): 609-19.

Lian et al., Trends and developments in liposome drug delivery systems. J Pharm Sci. Jun. 2001;90(6):667-80.

Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.

Lindgren et al., Induction of Robust B Cell Responses after Influenza mRNA Vaccination is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.

Lorenzi et al., Intranasal vaccination with messenger RNA as a new approach in gene therapy: Use against tuberculosis. BMC Biotechnol. Oct. 2010; 10(77): 1-11.

Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.

Madden et al., Administration of nucleoside-modified mRNA encoding broadly neutralizing antibody protects humanized mice from HIV-1 challenge. Nat Commun. Mar. 2, 2017;8:14630. doi: 10.1038/ncomms14630. Available at https://acuitastx.com/wp-content/uploads/2015/01/Poster-Second-International-mRNA-Health-Conference.pdf.

Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.

Martinon et al., Induction of virus-specific cytotoxic T lymphocytes in vivo by liposome-entrapped mRNA. EurJ Immunol. Jul. 1993;23(7):1719-22.

McKenzie et al., Nucleic acid vaccines: tasks and tactics. Immunol Res. 2001;24(3):225-44.

McSweegan et al., The Global Virus Network: Challenging chikungunya. Antiviral Res. Aug. 2015;120:147-52. doi: 10.1016/j.antiviral.2015.06.003. Epub Jun. 10, 2015.

Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.

(56) References Cited

OTHER PUBLICATIONS

Mitchell et al., RNA transfected dendritic cells as cancer vaccines. Curr Opin Mal Ther. Apr. 2000;2(2):176-81.

Mitchell et al., RNA-transfected dendritic cells in cancer immunotherapy. J Clin Invest. Nov. 2000;106 (9):1065-9.

Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.

Muller et al., Transfection of dendritic cells with RNA induces CD4- and COB-mediated T cell immunity against breast carcinomas and reveals the immunodominance of presented T cell epitopes. J lmmunol. Jun. 15, 2003;170 (12):5892-6.

Pardi et al., Zika virus protection by a single low-dose nucleoside-modified mRNA vaccination. Nature. Mar. 9, 2017;543(7644):248-251. doi: 10.1038/nature21428. Epub Feb. 2, 2017.

Parisien et al., Rationalization and prediction of selective decoding of pseudouridine-modified nonsense and sense codons. RNA. Mar. 2012;18(3):355-67. doi: 10.1261/rna.031351.111. Epub Jan. 26, 2012.

Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.

Phua et al., Messenger RNA (mRNA) nanoparticle tumour vaccination. Nanoscale. Jul. 21, 2014;6(14):7715-29. doi: 10.1039/c4nr01346h. Review.

Pollard et al., Type I IFN counteracts the induction of antigen-specific immune responses by lipid-based delivery of mRNA vaccines. Mol Ther. Jan. 2013; 21 (1): 251-259.

Pulford et al., Liposome-siRNA-peptide complexes cross the blood-brain barrier and significantly decrease PrP'C on neuronal cells and PrP'RES in infected cell cultures. PLoS ONE. 201 O; 5(6): e11085.

Rabinovich et al., Synthetic messenger RNA as a tool for gene therapy. Hum. Gene Ther. Oct. 2006; 17: 1027-1035.

Richner et al., Modified mRNA Vaccines Protect against Zika Virus Infection. Cell. Mar. 23, 2017;169(1):176. doi: 10.1016/j.cell.2017.03.016.

Richner et al., Vaccine Mediated Protection Against Zika Virus-Induced Congenital Disease. Cell. Jul. 13, 2017;170(2):273-283.e12. doi: 10.1016/j.cell.2017.06.040.

Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.

Schirrmacher et al., Intra-pinna anti-tumor vaccination with self-replicating infectious RNA or with DNA encoding a model tumor antigen and a cytokine. Gene Ther. Jul. 2000;7(13):1137-47.

Schmitt et al., In vitro induction of a bladder cancer-specific T-cell response by mRNA-transfected dendritic cells. J Cancer Res Clin Oncol. 2001;127(3):203-6.

Schott et al., Viral and non-viral approaches for transient delivery of mRNA and proteins. Current Gene Ther. 2011; 11 (5): 382-398.

Segura et al., Monitoring gene therapy by external imaging of mRNA: Pilot study on murine erythropoietin. Ther Drug Monit. Oct. 2007; 29(5): 612-8.

Smits et al. RNA-based gene transfer for adult stem cells and T cells. Leukemia. 2004; 18: 1898-1902.

Sohn et al., In-vivo particle mediated delivery of mRNA to mammalian tissues: ballistic and biological effects. Wound Rep and Regen. Jul.-Aug. 2001; 287-296.

Strong et al., Incorporation of beta-globin untranslated regions into a Sindbis virus vector for augmentation of heterologous mRNA expression. Gene Ther. Jun. 1997;4(6):624-7.

Sullenger et al., Emerging clinical applications of RNA. Nature. Jul. 11, 2002;418(6894):252-8.

Tavernier et al., mRNA as gene therapeutic: How to control protein expression. J. of Controlled Release. Mar. 2011; 150(3): 238-247.

Tekmira, Lipid Nanoparticle-mediated delivery of messenger RNA (retrieved from the internet). Published Oct. 24, 2013. Available at http://files.shareholder.com/downloads/ABEA-50QJTB/2628241206x0x699789/47543d12-db34-4e6e-88a9-f3ae5d97b1d2/MacLachlan_mRNA_Conf_2013.pdf.

Teufel et al., Human peripheral blood mononuclear cells transfected with messenger RNA stimulate antigen-specific cytotoxic T-lymphocytes in vitro. Cell Mol Life Sci. Aug. 2005;62(15):1755-62.

Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.

Vassilev et al., Microparticle-mediated RNA immunization against bovine viral diarrhea virus. Vaccine. Feb. 28, 2001;19(15-16):2012-9.

Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Wong et al., An mRNA vaccine for influenza. Nat Biotechnol. Dec. 2012;30(12):1202-4. doi: 10.1038/nbt.2439.

Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.

Ying et al., Cancer therapy using a self-replicating RNA vaccine. Nat Med. Jul. 1999;5(7):823-7.

Zhou et al., RNA melanoma vaccine: induction of antitumor immunity by human glycoprotein 100 mRNA immunization. Hum Gene Ther. Nov. 1, 1999;10(16):2719-24.

U.S. Appl. No. 16/450,882, filed Jun. 24, 2019, Ciaramella.
U.S. Appl. No. 15/767,710, filed Apr. 19, 2018, Ciaramella et al.
U.S. Appl. No. 16/229,509, filed Dec. 21, 2018, Besin et al.
U.S. Appl. No. 16/333,330, filed Mar. 14, 2019, Hoge et al.
U.S. Appl. No. 16/389,545, filed Apr. 19, 2019, Ciaramella et al.
U.S. Appl. No. 16/368,099, filed Mar. 28, 2019, Ciaramella et al.
U.S. Appl. No. 16/368,270, filed Mar. 28, 2019, Ciaramella et al.
U.S. Appl. No. 16/468,838, filed Jun. 12, 2019, Miracco.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/482,844, filed Aug. 1, 2019, Valiante et al.
U.S. Appl. No. 16/483,012, filed Aug. 1, 2019, Mauger et al.
U.S. Appl. No. 16/432,541, filed Jun. 5, 2019, Rabideau et al.
U.S. Appl. No. 16/362,366, filed Mar. 22, 2019, Ciaramella.
PCT/US2018/051120, Dec. 24, 2018, International Search Report and Written Opinion.

ZIKA VIRUS MRNA VACCINES

RELATED APPLICATIONS

This application claims the benefit under 35 U.S.C. § 119(e) of U.S. provisional application No. 62/558,746, filed Sep. 14, 2017, which is incorporated by reference herein in its entirety.

BACKGROUND

Zika virus (ZIKV) was identified in 1947 from a sentinel Rhesus monkey in the Zika Forest of Uganda. Historically, ZIKV circulated between *Aedes* species mosquitoes, non-human primates in the jungle, and episodically spilled into human populations in Africa and parts of Southeast Asia. Infection was associated with a mild, self-limiting febrile illness characterized by headache, rash, conjunctivitis, myalgia, and arthralgia. Since 2010, and especially in the context of its spread and dissemination to countries of the Western Hemisphere, more severe clinical consequences have been observed. Infection of fetuses in utero during pregnancy, particularly during the first and second trimesters, has been associated with placental insufficiency and congenital malformations including cerebral calcifications, microcephaly, and miscarriage. In adults, ZIKV infection is linked to an increased incidence of Guillain-Barré syndrome (GBS), an autoimmune disease characterized by paralysis and polyneuropathy. In addition to mosquito and in utero transmission, sexual transmission of ZIKV has been described from men-to-women, men-to-men, and women-to-men. Persistent ZIKV infection can occur, as viral RNA has been detected in semen, sperm, and vaginal secretions up to 6 months following infection. Thus, ZIKV is now a global disease with locally-acquired and travel-associated transmission through multiple routes in the Americas, Africa, and Asia. The emergence of ZIKV infection has prompted a global effort to develop safe and effective vaccines.

SUMMARY

Experimental results provided herein demonstrate an unexpected improvement in efficacy with Zika virus (ZIKV) RNA vaccines encoding a Japanese encephalitis virus (JEV) signal peptide fused to a ZIKV prME protein. As shown in the Examples, the ZIKV mRNA vaccine encoding a JEV signal peptide fused to prME unexpectedly provided sterilizing immunity in non-human primates at a 20-fold lower dose relative to a ZIKV mRNA vaccine encoding a IgE signal peptide fused to prME.

Thus, in some aspects, provided herein are RNA vaccines that comprise a 5' UTR, an ORF encoding a JEV signal peptide fused to a ZIKV prME protein, and a 3' UTR. In some embodiments, the 5' UTR is selected from SEQ ID NO:13 and SEQ ID NO:14. In some embodiments, the ORF comprises a sequence selected from SEQ ID NOs:1-6. In some embodiments, the 3' UTR is selected from SEQ ID NO:15 and SEQ ID NO:16. In some embodiments, the JEV signal peptide comprises the following sequence: MWLVS-LAIVTACAGA (SEQ ID NO:18). In some embodiments, the JEV signal peptide is encoded by the following sequence: AUGUGGCUGGUGUCCCUGGC-CAUCGUGACA GCCUGUGCUGGCGCC (SEQ ID NO:19).

Also provided herein are methods comprising administering to a subject a RNA vaccine comprising an open reading frame (ORF) encoding a JEV signal peptide fused to a ZIKV prME protein in an effective amount to induce in the subject a ZIKV prME-specific immune response, wherein the effective amount is sufficient to provide sterilizing immunity in the subject at an at least 10-fold lower dose relative to a ZIKV mRNA vaccine encoding a IgE signal peptide fused to prME. In some embodiments, the effective amount is sufficient to provide sterilizing immunity in the subject at an at least 20-fold lower dose relative to a ZIKV mRNA vaccine encoding a IgE signal peptide fused to prME.

In some aspects, the methods comprise administering to a subject a RNA vaccine comprising an ORF encoding a JEV signal peptide fused to a ZIKV prME protein in an effective amount to reduce viral load in the subject by at least 80%, relative to a control, at 3-7 days following exposure to ZIKV, wherein the control is the viral load in a subject administered a ZIKV RNA vaccine lacking the JEV signal sequence.

In other aspects, the methods comprise administering to a subject a RNA vaccine comprising an ORF encoding a JEV signal peptide fused to a ZIKV prME protein in an effective amount to induce in the subject a ZIKV prME-specific immune response, wherein efficacy of the RNA vaccine is at least 80% relative to unvaccinated control subjects.

DETAILED DESCRIPTION

Figure 1:
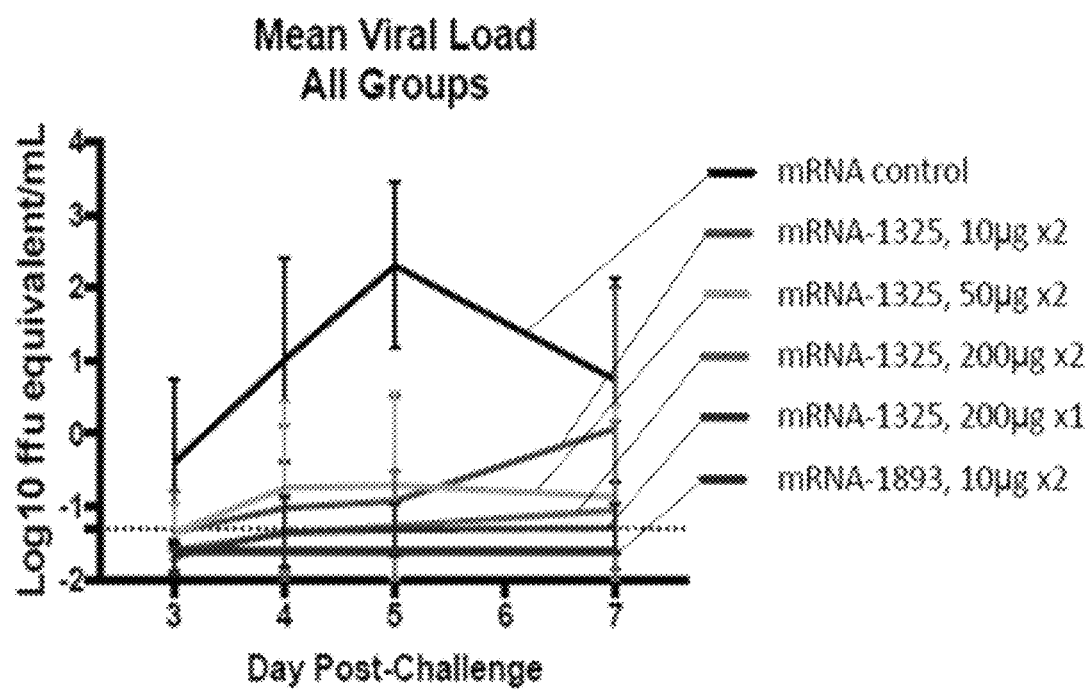
FIG. 1 is a graph showing the viral yield ($\log_{10}$ focus forming units (FFU)/ml) 3, 4, 5, 6 and 7 days post challenge (with ZIKV) in non-human primates (NHPs) vaccinated with 10 µg, 50 µg, or 200 µg ZIKV mRNA vaccine. Vaccine 'mRNA-1325' encodes an IgE signal peptide fused to ZIKV prME. Vaccine 'mRNA-1893' encodes a JEV signal peptide fused to ZIKV prME. A single 200 µg dose of the mRNA-1325 vaccine confers nearly complete protection. Unexpectedly, the mRNA-1893 vaccine outperforms the mRNA-1325 vaccine in this model by at least 20×.

Zika virus (ZIKV) is a member of the Flaviviridae virus family and the flavivirus genus. In humans, it causes a disease known as Zika fever. It is related to dengue, yellow fever, West Nile and Japanese encephalitis, viruses that are also members of the virus family Flaviviridae. ZIKV is spread to people through mosquito bites. The most common symptoms of ZIKV disease (Zika) are fever, rash, joint pain, and red eye. The illness is usually mild with symptoms lasting from several days to a week. There is no vaccine to prevent, or medicine to treat ZIKV.

Provided herein, in some embodiments, are ZIKV ribonucleic acid (RNA) vaccines (e.g., mRNA vaccines) comprising a 5' untranslated region (UTR), an open reading frame (ORF) encoding a JEV signal peptide fused to a ZIKV prME protein, and a 3' UTR. In some embodiments, the ZIKV RNA vaccines comprise a polyA tail.

A 5' UTR is region of an mRNA that is directly upstream (5') from the start codon (the first codon of an mRNA transcript translated by a ribosome). A 5' UTR does not encode a polypeptide (is non-coding). In some embodiments, a 5' UTR of the present disclosure comprises a sequence selected from SEQ ID NO:13 and SEQ ID NO:14.

A 3' UTR is region of an mRNA that is directly downstream (3') from the stop codon (the codon of an mRNA transcript that signals a termination of translation) A 3' UTR does not encode a polypeptide (is non-coding). In some embodiments, a 3' UTR of the present disclosure comprises a sequence selected from SEQ ID NO:15 and SEQ ID NO:16.

A polyA tail is a region of mRNA that is downstream, e.g., directly downstream, from the 3' UTR and contains multiple, consecutive adenosine monophosphates. In a relevant biological setting (e.g., in cells, in vivo), the polyA tail functions to protect mRNA from enzymatic degradation, e.g., in the cytoplasm, and aids in transcription termination, export of the mRNA from the nucleus, and translation. A polyA tail may comprise, for example, 10 to 300 adenosine monophosphates. For example, a polyA tail may comprise 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail comprises 50 to 250 adenosine monophosphates. In some embodiments, a polyA tail comprises 100 adenosine monophosphates.

In some embodiments, the ZIKV RNA vaccine comprises 5' terminal cap, for example, 7mG(5')ppp(5')NlmpNp.

An open reading frame is a continuous stretch of DNA or RNA beginning with a start codon (e.g., methionine (ATG or AUG)) and ending with a stop codon (e.g., TAA, TAG or TGA, or UAA, UAG or UGA). In some embodiments, an ORF of the present disclosure is selected from SEQ ID NO:1, SEQ ID NO:2, SEQ ID NO:3, SEQ ID NO:4, SEQ ID NO:5, and SEQ ID NO:6. In some embodiments, the ORF comprises the sequence of SEQ ID NO:1. In some embodiments, the ORF comprises the sequence of SEQ ID NO:2. In some embodiments, the ORF comprises the sequence of SEQ ID NO:3. In some embodiments, the ORF comprises the sequence of SEQ ID NO:4. In some embodiments, the ORF comprises the sequence of SEQ ID NO:5. In some embodiments, the ORF comprises the sequence of SEQ ID NO:6.

The ZIKV RNA vaccines (e.g., mRNA vaccines) of the present disclosure encode a JEV signal peptide (e.g., SEQ ID NO:18) fused (in frame) to a ZIKV prME protein. The particular prME sequence may be from any ZIKV strain, for example those strains as are known in the art or as otherwise described herein, such as a Brazilian strain, a Micronesian strain, or an African strain. Within the Zika family, there is a high level of homology within the prME sequence (>90%) across all strains so far isolated. The high degree of homology is also preserved when comparing the original isolates from 1947 to the more contemporary strains circulating in Brazil in 2015, suggesting that there is "drift" occurring from the original isolates. Furthermore, attenuated virus preparations have provided cross-immunization to all other strains tested, including Latin American/Asian, and African. Overall, this data suggests that cross-protection of all Zika strains is possible with a vaccine based on prME. In fact, the prM/M and E proteins of ZIKV have a very high level (99%) of sequence conservation between the currently circulating Asiatic and Brazilian viral strains.

The M and E proteins are on the surface of the viral particle. Neutralizing antibodies predominantly bind to the E protein, the preM/M protein functions as a chaperone for proper folding of E protein and prevent premature fusion of E protein within acidic compartments along the cellular secretory pathway.

In some embodiments, the ZIKV prME protein comprises a sequence selected from SEQ ID NO:7, SEQ ID NO:8, SEQ ID NO:9, SEQ ID NO:10, SEQ ID NO:11, and SEQ ID NO:12. In some embodiments, the ZIKV prME protein comprises the sequence of SEQ ID NO:7. In some embodiments, the ZIKV prME protein comprises the sequence of SEQ ID NO:8. In some embodiments, the ZIKV prME protein comprises the sequence of SEQ ID NO:9. In some embodiments, the ZIKV prME protein comprises the sequence of SEQ ID NO:10. In some embodiments, the ZIKV prME protein comprises the sequence of SEQ ID NO:11. In some embodiments, the ZIKV prME protein comprises the sequence of SEQ ID NO:12.

ZIKV RNA vaccines (e.g., mRNA vaccines) of the present disclosure encode a JEV signal peptide fused to a prME protein. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane. In some embodiments, the JEV signal peptide of the present disclosure comprises the sequence of SEQ ID NO:18.

In some embodiments, a RNA (e.g., mRNA) of a ZIKV RNA vaccine of the present disclosure is chemically modified. For example, at least 80% of the uracil in the ORF may have a chemical modification selected from N1-methyl-pseudouridine and N1-ethyl-pseudouridine. In some embodiments, at least 85%, at least 90%, at least 95% or 100% of the uracil in the ORF have a chemical modification. In some embodiments, the chemical modification is in the 5-position of the uracil.

In some embodiments, at least one RNA (e.g., mRNA) of the ZIKV RNA vaccines of the present disclosure are not chemically modified, and comprise the standard ribonucleotides consisting of adenosine, guanosine, cytosine and uridine.

ZIKV RNA vaccines (e.g., mRNA vaccines) of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid. In some embodiments, the lipid nanoparticle comprises a molar ratio of 20-60% ionizable cationic lipid, 5-25% non-cationic lipid, 25-55% sterol, and 0.5-15% PEG-modified lipid. In some embodiments, the ionizable cationic lipid comprises the following compound:

Data provided herein demonstrates that ZIKV mRNA vaccines encoding a JEV signal peptide fused to prME provide sterilizing immunity in non-human primates at a 20-fold lower dose relative to a ZIKV mRNA vaccine encoding a IgE signal peptide fused to prME. Thus, provided herein, in some embodiments, are methods comprising administering to a subject a RNA vaccine comprising an ORF encoding a JEV signal peptide fused to a ZIKV prME protein in an effective amount to induce in the subject a ZIKV prME-specific immune response, wherein the effective amount is sufficient to provide sterilizing immunity in the subject at an at least 5-fold lower dose relative to a ZIKV mRNA vaccine encoding a IgE signal peptide fused to prME. In some embodiments, the effective amount is sufficient to provide sterilizing immunity in the subject at an at least 10-fold lower dose relative to a ZIKV mRNA vaccine encoding a IgE signal peptide fused to prME. the effective amount is sufficient to provide sterilizing immunity in the subject at an at least 15-fold lower dose relative to a ZIKV mRNA vaccine encoding a IgE signal peptide fused to prME. the effective amount is sufficient to provide sterilizing immunity in the subject at an at least 20-fold lower dose relative to a ZIKV mRNA vaccine encoding a IgE signal peptide fused to prME.

A subject may be any mammal, including non-human primate and human subjects. Typically, a subject is a human subject.

In some embodiments, methods of the present disclosure comprise administering to a subject a RNA vaccine comprising an ORF encoding a JEV signal peptide fused to a ZIKV prME protein in an effective amount to reduce viral load in the subject by at least 80%, relative to a control (e.g., at 3-7 days following exposure to ZIKV), wherein the control is the viral load in a subject administered a ZIKV RNA vaccine lacking the JEV signal sequence. In some embodiments, the amount of ZIKV RNA vaccine administered is effective to reduce viral load in the subject by at least 85%, at least 90%, at least 95%, at least 98% or 100%. In some embodiments, the control is the viral load in a subject administered a ZIKV RNA vaccine containing an IgE signal sequence. In some embodiments, the control is the viral load in an unvaccinated subject.

In some embodiments, the methods comprise administering to a subject ZIKV vaccine comprising an ORF encoding a JEV signal peptide fused to a ZIKV prME protein in an effective amount to induce in the subject a ZIKV prME-specific immune response, wherein efficacy of the RNA vaccine is at least 60% relative to unvaccinated control subjects. For example, the efficacy of the ZIKV RNA vaccine may be at least 65%, at least 70%, at least 75%, at least 80%, at least 85%, at least 90%, or at least 98%, relative to unvaccinated control subjects. In some embodiments, the efficacy of the RNA vaccine is at least 80% relative to unvaccinated control subjects. In some embodiments, the efficacy of the RNA vaccine is at least 95% relative to unvaccinated control subjects.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

Efficacy=(ARU−ARV)/ARU×100; and

Efficacy=(1−RR)×100.

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

Effectiveness=(1−OR)×100.

In some embodiments, the effective amount of a ZIKV RNA vaccine is sufficient to produce detectable levels of ZIKV prME protein as measured in serum of the subject at 1-72 hours post administration.

In some embodiments, the effective amount of a ZIKV RNA vaccine amount is sufficient to produce a 1,000-10,000 neutralization titer produced by neutralizing antibody against the ZIKV prME protein as measured in serum of the subject at 1-72 hours post administration. In some embodiments, the effective amount of a ZIKV RNA vaccine amount is sufficient to produce a 1,000-5,000 neutralization titer produced by neutralizing antibody against the ZIKV prME protein as measured in serum of the subject at 1-72 hours post administration. In some embodiments, the effective amount of a ZIKV RNA vaccine amount is sufficient to produce a 5,000-10,000 neutralization titer produced by neutralizing antibody against the ZIKV prME protein as measured in serum of the subject at 1-72 hours post administration.

In some embodiments, an anti-ZIKV prME protein antibody titer produced in a subject administered a ZIKV RNA vaccine is increased by at least 1 log relative to a control, wherein the control is an anti-ZIKV prME protein antibody titer produced in a subject who has not been administered a vaccine against ZIKV. In some embodiments, an anti-ZIKV prME protein antibody titer produced in a subject administered a ZIKV RNA vaccine is increased by at least 2 log relative to the control. In some embodiments, an anti-ZIKV prME protein antibody titer produced in a subject administered a ZIKV RNA vaccine is increased by at least 5 log relative to the control. In some embodiments, an anti-ZIKV prME protein antibody titer produced in a subject administered a ZIKV RNA vaccine is increased by at least 10 log relative to the control.

In some embodiments, an anti-ZIKV prME protein antibody titer produced in a subject is increased at least 2 times relative to a control, wherein the control is an anti-ZIKV prME protein antibody titer produced in a subject who has not been administered a vaccine against ZIKV. In some embodiments, an anti-ZIKV prME protein antibody titer produced in a subject is increased at least 5 times relative to a control. In some embodiments, an anti-ZIKV prME protein antibody titer produced in a subject is increased at least 10 times relative to a control.

The effective amount of a ZIKV RNA vaccine (e.g., mRNA vaccine), as provided herein, surprisingly may be as low as 20 µg, administered for example as a single dose or as two 10 µg doses. In some embodiments, the effective amount is 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95

μg, 100 μg, 110 μg, 120 μg, 130 μg, 140 μg, 150 μg, 160 μg, 170 μg, 180 μg, 190 μg or 200 μg. In some embodiments, the effective amount is a total dose of 25 μg-200 μg.

Table 1 below provides examples of ZIKV mRNA vaccine sequences and corresponding protein sequences encoded by the vaccines.

TABLE 1

ZIKV mRNA Vaccine Sequences

| ORF (with JEV signal sequence underlined) | Protein (with JEV signal sequence underlined) |
|---|---|
| ZIKV prME Brazil Isolate (mRNA) <br> <u>AUGUGGCUGGUGUCCCUGGCCAUCGUGACA</u> <br> <u>GCCUGUGCUGGCGCCGCUGAAGUGACCAGA</u> <br> AGAGGCAGCGCCUACUACAUGUACCUGGAC <br> CGGAACGAUGCCGGCGAGGCCAUCAGCUUU <br> CCAACCACCCUGGGCAUGAACAAGUGCUAC <br> AUCCAGAUCAUGGACCUGGGCCACAUGUGC <br> GACGCCACCAUGAGCUACGAGUGCCCCAUG <br> CUGGACGAGGGCGUGGAACCCGACGAUGUG <br> GACUGCUGGUGCAACACCACCAGCACCUGG <br> GUGGUGUACGGCACCUGUCACCACAAGAAG <br> GGCGAAGCCAGACGUCCAGACGGGCCGUG <br> ACACUGCCUAGCCACAGCACCAGAAAGCUG <br> CAGACCCGGUCCCAGACCUGGCUGGAAAGC <br> AGAGAGUACACCAAGCACCUGAUCCGGGUG <br> GAAAACUGGAUCUUCCGGAACCCCGGCUUU <br> GCCCUGGCCGCUGCUGCUAUUGCUUGGCUG <br> CUGGGCAGCAGCACCUCCCAGAAAGUGAUC <br> UACCUCGUGAUGAUCCUGCUGAUCGCCCCU <br> GCCUACAGCAUCCGGUGUAUCGGCGUGUCC <br> AACCGGGACUUCGUGGAAGGCAUGAGCGGC <br> GGCACAUGGGUGGACGUGGUGCUGGAACAU <br> GGCGGCUGCGUGACAGUGAUGGCCCAGGAC <br> AAGCCCACCGUGGACAUCGAGCUCGUGACC <br> ACCACCGUGUCCAAUAUGGCCGAAGUGCGG <br> AGCUACUGCUACGAGGCCAGCAUCAGCGAC <br> AUGGCCGACAGCAGAUGCCCUACACAG <br> GGCGAGGCCUACCUGGACAAGCAGUCCGAC <br> ACCCAGUACGUGUGCAAGCGGACCCUGGUG <br> GAUAGAGGCUGGGGCAAUGGCUGCGGCCUG <br> UUUGGCAAGGGCAGCCUCGUGACCUGCGCC <br> AAGUUCGCCUGCAGCAAGAAGAUGACCGGC <br> AAGAGCAUCCAGCCCGAGAACCUGGAAUAC <br> CGGAUCAUGCUGAGCGUGCACGGCAGCCAG <br> CACUCCGGCAUGAUCGUGAACGACACCGGC <br> CACGAGACAGACGAGAACCGGGCCAAGGUG <br> GAAAUCACCCCUAACAGCCCUAGAGCCGAG <br> GCCACACUGGGCGGCUUUGGAUCUCUGGGC <br> CUGGACUGCGAGCCUAGAACCGGCCUGGAU <br> UUCAGCGACCUGUACUACCUGACCAUGAAC <br> AACAAGCACUGGCUGGUGCACAAAGAGUGG <br> UUCCACGACAUCCCUCUGCCCUGGCAUGCC <br> GGCGCUGAUACAGGCACACCCCACUGGAAC <br> AACAAAGAGGCUCUGGUGGAAUUCAAGGAC <br> GCCCACGCCAAGCGGCAGACCGUGGUGGUG <br> CUGGGAUCUCAGGAAGGCGCCGUGCAUACA <br> GCUCUGGCAGGCGCCCUGGAAGCCGAAAUG <br> GAUGGCGCCAAAGGCAGACUGUCCAGCGGC <br> CACCUGAAGUGCCGGCUGAAGAUGGACAAG <br> CUGCGGCUGAAGGGCGUGUCCUACUCCCUG <br> UGUACCGCCGCCUUCACCUUCACCAAGAUC <br> CCCGCCGAGACACUGCACGGCACCGUGACU <br> GUGGAAGUGCAGUACGCCGGCACCGACGGC <br> CCUUGUAAAGUGCCUGCUCAGAUGGCCGUG <br> GAUAUGCAGACCCUGACCCCUGUGGGCAGA <br> CUGAUCACCGCCAACCCCGUGAUCACCGAG <br> AGCACCGAGAACAGCAAGAUGAUGCUGGAA <br> CUGGACCCACCCUUCGGCGACAGCUACAUC <br> GUGAUCGGCGUGGGAGAGAAGAAGAUCACC <br> CACCACUGGCACAGAAGCGGCAGCACCAUC <br> GGCAAGGCCUUUGAGGCUACAGUGCGGGGA <br> GCCAAGAGAAUGGCCGUGCUGGGAGAUACC <br> GCCUGGGACUUUGGCUCUGUGGGCGGAGCC <br> CUGAACUCUCUGGGCAAGGGAAUCCACCAG <br> AUCUUCGGAGCCGCCUUUAAGAGCCUGUUC <br> GGCGGCAUGAGCUGGUUCAGCCAGAUCCUG <br> AUCGGCACCCUGCUGAUGUGGCUGGGCCUG <br> AACACCAAGAACGGCAGCAUCUCCCUGAUG <br> UGCCUGGCUCUGGGAGGCGUGCUGAUCUUC <br> CUGAGCACAGCCGUGUCUGCC (SEQ ID NO: 1) | ZIKV prME Brazil Isolate (protein) <br> <u>MWLVSLAIVTACAGAAEVTRRGSAYYMYLDR</u> <br> NDAGEAISFPTTLGMNKCYIQIMDLGHMCDAT <br> MSYECPMLDEGVEPDDVDCWCNTTSTWVVY <br> GTCHHKKGEARRSRRAVTLPSHSTRKLQTRSQ <br> TWLESREYTKHLIRVENWIFRNPGFALAAAAIA <br> WLLGSSTSQKVIYLVMILLIAPAYSIRCIGVSNR <br> DFVEGMSGGTWVDVVLEHGGCVTVMAQDKP <br> TVDIELVTTTVNMAEVRSYCYEASISDMASDS <br> RCPTQGEAYLDKQSDTQYVCKRTLVDRGWGN <br> GCGLFGKGSLVTCAKFACSKKMTGKSIQPENL <br> EYRIMLSVHGSQHSGMIVNDTGHETDENRAKV <br> EITPNSPRAEATLGGFGSLGLDCEPRTGLDFSDL <br> YYLTMNNKHWLVHKEWFHDIPLPWHAGADT <br> GTPHWNNKEALVEFKDAHAKRQTVVVLGSQE <br> GAVHTALAGALEAEMDGAKGRLSSGHLKCRL <br> KMDKLRLKGVSYSLCTAAFTFTKIPAETLHGT <br> VTVEVQYAGTDGPCKVPAQMAVDMQTLTPV <br> GRLITANPVITESTENSKMMLELDPPFGDSYIVI <br> GVGEKKITHHWHRSGSTIGKAFEATVRGAKR <br> MAVLGDTAWDFGSVGGALNSLGKGIHQIFGA <br> AFKSLFGGMSWFSQILIGTLLMWLGLNTKNGSI <br> SLMCLALGGVLIFLSTAVSA (SEQ ID NO: 7) |

TABLE 1-continued

ZIKV mRNA Vaccine Sequences

| ORF (with JEV signal sequence underlined) | Protein (with JEV signal sequence underlined) |
|---|---|
| ZIKV prME Brazil Isolate (mRNA), with T76R, Q77E, W101R, L107R mutations<br><u>AUGUGGCUGGUGUCCCUGGCCAUCGUGACA</u><br><u>GCCUGUGCUGGCGCC</u>GCUGAAGUGACCAGA<br>AGAGGCAGCGCCUACUACAUGUACCUGGAC<br>CGGAACGAUGCCGGCGAGGCCAUCAGCUUU<br>CCAACCACCCUGGGCAUGAACAAGUGCUAC<br>AUCCAGAUCAUGGACCUGGGCCACAUGUGC<br>GACGCCACCAUGAGCUACGAGUGCCCCAUG<br>CUGGACGAGGGCGUGGAACCCGACGAUGUG<br>GACUGCUGGUGCAACACCACCAGCACCUGG<br>GUGGUGUACGGCACCUGUCACCACAAGAAG<br>GGCGAAGCCAGACGGUCCAGACGGGCCGUG<br>ACACUGCCUAGCCACAGCACCAGAAAGCUG<br>CAGACCCGGUCCCAGACCUGGCUGGAAAGC<br>AGAGAGUACACCAAGCACCUGAUCCGGGUG<br>GAAAACUGGAUCUUCCGGAACCCCGGCUUU<br>GCCCUGGCCGCUGCUGCUAUUGCUUGGCUG<br>CUGGGCAGCAGCACCUCCCAGAAAGUGAUC<br>UACCUCGUGAUGAUCCUGCUGAUCGCCCCU<br>GCCUACAGCAUCCGGUGUAUCGGCGUGUCC<br>AACCGGGACUUCGUGGAAGGCAUGAGCGGC<br>GGCACAUGGGUGGACGUGGUGCUGGAACAU<br>GGCGGCUGCGUGACAGUGAUGGCCCAGGAC<br>AAGCCCACCGUGGACAUCGAGCUCGUGACC<br>ACCACCGUGUCCAAUAUGGCCGAAGUGCGG<br>AGCUACUGCUACGAGGCCAGCAUCAGCGAC<br>AUGGCCAGCGACAGCAGAUGCCCCAGAGAG<br>GGCGAGGCCUACCUGGACAAGCAGUCCGAC<br>ACCCAGUACGUGUGCAAGCGGACCCUGGUG<br>GACAGAGGCAGAGGCAAUGGCUGCGGCAGA<br>UUCGGCAAGGGCAGCCUCGUGACCUGCGCC<br>AAGUUCGCCUGCAGCAAGAAGAUGACCGGC<br>AAGAGCAUCCAGCCCGAGAACCUGGAAUAC<br>CGGAUCAUGCUGAGCGUGCACGGCAGCCAG<br>CACUCCGGCAUGAUCGUGAACGACACCGGC<br>CACGAGACAGACGAGAACCGGGCCAAGGUG<br>GAAAUCACCCCUAACAGCCCUAGAGCCGAG<br>GCCACACUGGGCGGCUUUGGAUCUCUGGGC<br>CUGGACUGCGAGCCUAGAACCGGCCUGGAU<br>UUCAGCGACCUGUACUACCUGACCAUGAAC<br>AACAAGCACUGGCUGGUGCACAAAGAGUGG<br>UUCCACGACAUCCCUCUGCCCUGGCAUGCC<br>GGCGCUGAUACAGGCACACCCCACUGGAAC<br>AACAAAGAGGCUCUGGUGGAAUUCAAGGAC<br>GCCCACGCCAAGCGGCAGACCGUGGUGGUG<br>CUGGGAUCUCAGGAAGGCGCCGUGCAUACA<br>GCUCUGGCAGGCGCCCUGGAAGCCGAAAUG<br>GAUGGCGCCAAAGGCAGACUGUCCAGCGGC<br>CACCUGAAGUGCCGGCUGAAGAUGGACAAG<br>CUGCGGCUGAAGGGCGUGUCCUACUCCCUG<br>UGUACCGCCGCCUUCACCUUCACCAAGAUC<br>CCCGCCGAGACACUGCACGGCACCGUGACU<br>GUGGAAGUGCAGUACGCCGGCACCGACGGC<br>CCUUGUAAAGUGCCUGCUCAGAUGGCCGUG<br>GAUAUGCAGACCCUGACCCCUGUGGGCAGA<br>CUGAUCACCGCCAACCCCGUGAUCACCGAG<br>AGCACCGAGAACAGCAAGAUGAUGCUGGAA<br>CUGGACCCACCCUUCGGCGACAGCUACAUC<br>GUGAUCGGCGUGGGAGAGAAGAAGAUCACC<br>CACCACUGGCACAGAAGCGGCAGCACCAUC<br>GGCAAGGCCUUUGAGGCUACAGUGCGGGGA<br>GCCAAGAGAAUGGCCGUGCUGGGAGAUACC<br>GCCUGGGACUUUGGCUCUGUGGGCGGAGCC<br>CUGAACUCUCUGGGCAAGGGAAUCCACCAG<br>AUCUUCGGAGCCGCCUUUAAGAGCCUGUUC<br>GGCGGCAUGAGCUGGUUCAGCCAGAUCCUG<br>AUCGGCACCCUGCUGAUGUGGCUGGGCCUG<br>AACACCAAGAACGGCAGCAUCUCCCUGAUG<br>UGCCUGGCUCUGGGAGGCGUGCUGAUCUUC<br>CUGAGCACAGCCGUGUCUGCC (SEQ ID NO: 2) | ZIKV prME Brazil Isolate (protein), with T76R, Q77E, W101R, L107R mutations<br><u>MWLVSLAIVTACAGAA</u>EVTRRGSAYYMYLDR<br>NDAGEAISFPTTLGMNKCYIQIMDLGHMCDAT<br>MSYECPMLDEGVEPDDVDCWCNTTSTWVVY<br>GTCHHKKGEARRSRRAVTLPSHSTRKLQTRSQ<br>TWLESREYTKHLIRVENWIFRNPGFALAAAAIA<br>WLLGSSTSQKVIYLVMILLIAPAYSIRCIGVSNR<br>DFVEGMSGGTWVDVVLEHGGCVTVMAQDKP<br>TVDIELVTTTVSNMAEVRSYCYEASISDMASDS<br>RCPREGEAYLDKQSDTQYVCKRTLVDRGRGN<br>GCGRFGKGSLVTCAKFACSKKMTGKSIQPENL<br>EYRIMLSVHGSQHSGMIVNDTGHETDENRAKV<br>EITPNSPRAEATLGGFGSLGLDCEPRTGLDFSDL<br>YYLTMNNKHWLVHKEWFHDIPLPWHAGADT<br>GTPHWNNKEALVEFKDAHAKRQTVVVLGSQE<br>GAVHTALAGALEAEMDGAKGRLSSGHLKCRL<br>KMDKLRLKGVSYSLCTAAFTFTKIPAETLHGT<br>VTVEVQYAGTDGPCKVPAQMAVDMQTLTPV<br>GRLITANPVITESTENSKMMLELDPPFGDSYIVI<br>GVGEKKITHHWHRSGSTIGKAFEATVRGAKR<br>MAVLGDTAWDFGSVGGALNSLGKGIHQIFGA<br>AFKSLFGGMSWFSQILIGTLLMWLGLNTKNGSI<br>SLMCLALGGVLIFLSTAVSA (SEQ ID NO: 8) |
| ZIKV prME Micronesia Isolate (mRNA)<br>AUGUGGCUGGUGAGCCUGGCCAUCGUGACC<br>GCCUGCGCCGGCGCCGUGGAGGUGACCAGA | ZIKV prME Micronesia Isolate (protein)<br><u>MWLVSLAIVTACAGA</u>VEVTRRGSAYYMYLDR<br>SDAGEAISFPTTLGMNKCYIQIMDLGHMCDAT |

TABLE 1-continued

ZIKV mRNA Vaccine Sequences

| ORF (with JEV signal sequence underlined) | Protein (with JEV signal sequence underlined) |
|---|---|
| AGAGGCAGCGCCUACUACAUGUACCUGGAC<br>AGAAGCGACGCCGGCGAGGCCAUCAGCUUC<br>CCUACCACCCUGGGCAUGAACAAGUGCUAC<br>AUCCAGAUCAUGGACCUGGGCCACAUGUGC<br>GACGCCACCAUGAGCUACGAGUGCCCUAUG<br>CUGGACGAGGGCGUGGAGCCUGACGACGUG<br>GACUGCUGGUGCAACACCACCAGCACCUGG<br>GUGGUGUACGGCACCUGCCACCACAAGAAG<br>GGAGAGGCGAGAAGAAGCAGGAGAGCCGUG<br>ACCCUGCCUAGCCACAGCACCAGAAAGCUG<br>CAGACCCGGAGCCAGACCUGGCUGGAGAGC<br>AGAGAGUACACCAAGCACCUGAUCAGAGUG<br>GAGAACUGGAUCUUCAGAAACCCUGGCUUC<br>GCCCUGGCCGCGGCUGCUAUCGCCUGGCUG<br>CUGGGUAGUUCAACCAGCCAGAAGGUGAUC<br>UACCUGGUGAUGAUCCUGCUGAUCGCCCCG<br>GCAUACAGCAUCCGCUGCAUCGGCGUGAGC<br>AACAGAGACUUCGUGGAGGGCAUGAGCGGA<br>GGAACGUGGGUUGACGUGGUGCUGGAGCAC<br>GGCGGCUGCGUGACCGUGAUGGCCCAGGAC<br>AAGCCUGCCGUGGACAUCGAGCUGGUGACC<br>ACCACCGUAUCCAACAUGGCCGAGGUGAGA<br>AGCUACUGCUACGAGGCUAGCAUAAGCGAC<br>AUGGCCAGCGACAGCCGAUGCCCUACCCAG<br>GGAGAAGCCUACCUGGACAAGCAGAGCGAC<br>ACCCAGUACGUGUGCAAGAGAACCCUGGUG<br>GACAGAGGCUGGGGCAACGGCUGCGGCCUG<br>UUCGGCAAGGGCAGCCUGGUUACUUGCGCC<br>AAGUUCGCCUGCAGCAAGAAGAUGACCGGC<br>AAGAGCAUCCAGCCUGAGAACCUGGAGUAC<br>AGAAUCAUGCUGAGCGUGCACGGCAGCCAG<br>CACAGCGGCAUGAUCGUGAACGACACCGGC<br>CACGAAACAGACGAGAACAGAGCCAAGGUG<br>GAGAUCACCCCUAACAGCCCUAGAGCCGAG<br>GCCACCCUUGGCGGCUUCGGCAGCCUCGGC<br>CUGGACUGCGAGCCUAGAACGGGCCUGGAU<br>UUCAGCGACCUGUACUACCUGACUAUGAAU<br>AACAAGCACUGGCUUGUUCAAGGAGUGG<br>UUCCACGACAUCCCUCUGCCUUGGCACGCG<br>GGAGCUGACACAGGAACCCCUCACUGGAAC<br>AACAAGGAGGCCCUAGUUGAGUUCAAGGAC<br>GCCCACGCCAAGAGACAGACCGUGGUCGUG<br>CUGGGUUCCCAAGAGGGCGCUGUCCACACU<br>GCACUCGCUGGCGCCCUGGAGGCCGAGAUG<br>GACGGCGCCAAGGGAAGACUGAGCAGCGGC<br>CACCUGAAGUGCAGGCUGAAGAUGGACAAG<br>CUGCGGCUGAAGGGCGUGUCCUACAGCCUG<br>UGCACCGCCGCCUUCACCUUCACCAAGAUC<br>CCUGCCGAGACACUACACGGCACAGUGACC<br>GUCGAGGUGCAGUACGCCGGCACCGACGGC<br>CCUUGCAAGGUGCCUGCCCAGAUGGCCGUC<br>GAUAUGCAAACUCUGACCCCUGUGGGACGG<br>CUUAUCACCGCCAACCCUGUGAUUACUGAG<br>AGCACCGAGAAUAGCAAGAUGAUGUUGGAA<br>CUGGACCCUCCUUUCGGCGACAGCUACAUC<br>GUGAUUGGAGUGGAGAGAAGAAGAUCAC<br>ACACCACUGGCACAGAUCUGGAUCUACUAU<br>UGGCAAGGCCUUCGAGGCAACAGUGAGAGG<br>AGCAAAGAGAAUGGCAGUUCUGGGAGACAC<br>CGCCUGGGAUUUCGGAAGCGUAGGAGGUGC<br>AUUGAACUCCUAGGAAAGGGAAUCCACCA<br>GAUCUUCGGAGCUGCAUUCAAGAGCCUAUU<br>CGGCGAAUGUCCUGGUUCAGCCAGAUCCU<br>GAUCGGCACCCUGCUUGUGUGGCUUGGAUU<br>GAACACCAAGAACGGUAGUAUUAGUCUGAC<br>CUGCCUGGCUCUCGGCGGUGUGCUGAUCUU<br>CCUGAGUACUGCGGUGAGCGCC (SEQ ID<br>NO: 3) | MSYECPMLDEGVEPDDVDCWCNTTSTWVVY<br>GTCHHKKGEARRSRRAVTLPSHSTRKLQTRSQ<br>TWLESREYTKHLIRVENWIFRNPGFALAAAAIA<br>WLLGSSTSQKVIYLVMILLIAPAYSIRCIGVSNR<br>DFVEGMSGGTWVDVVLEHGGCVTVMAQDKP<br>AVDIELVTTTVSNMAEVRSYCYEASISDMASD<br>SRCPTQGEAYLDKQSDTQYVCKRTLVDRGWG<br>NGCGLFGKGSLVTCAKFACSKKMTGKSIQPEN<br>LEYRIMLSVHGSQHSGMIVNDTGHETDENRAK<br>VEITPNSPRAEATLGGFGSLGLDCEPRTGLDFS<br>DLYYLTMNNKHWLVHKEWFHDIPLPWHAGA<br>DTGTPHWNNKEALVEFKDAHAKRQTVVVLGS<br>QEGAVHTALAGALEAEMDGAKGRLSSGHLKC<br>RLKMDKLRLKGVSYSLCTAAFTFTKIPAETLH<br>GTVTVEVQYAGTDGPCKVPAQMAVDMQTLTP<br>VGRLITANPVITESTENSKMMLELDPPFGDSYI<br>VIGVGEKKITHHWHRSGSTIGKAFEATVRGAK<br>RMAVLGDTAWDFGSVGGALNSLGKGIHQIFG<br>AAFKSLFGGMSWFSQILIGTLLVWLGLNTKNG<br>SISLTCLALGGVLIFLSTAVSA (SEQ ID NO: 9) |
| ZIKV prME Micronesia Isolate (mRNA), with<br>T76R, Q77E, W101R, L107R mutations<br>AUGUGGCUGGUGAGCCUGGCCAUCGUGACC<br>GCCUGCGCCGGCGCCGUGGAGGUGACCAGA<br>AGAGGCAGCGCCUACUACAUGUACCUGGAC<br>AGAAGCGACGCCGGCGAGGCCAUCAGCUUC<br>CCUACCACCCUGGGCAUGAACAAGUGCUAC | ZIKV prME Micronesia Isolate (protein),<br>with T76R, Q77E, W101R, L107R mutations<br>MWLVSLAIVTACAGAVEVTRRGSAYYMLDR<br>SDAGEAISFPTTLGMNKCYIQIMDLGHMCDAT<br>MSYECPMLDEGVEPDDVDCWCNTTSTWVVY<br>GTCHHKKGEARRSRRAVTLPSHSTRKLQTRSQ<br>TWLESREYTKHLIRVENWIFRNPGFALAAAAIA |

TABLE 1-continued

ZIKV mRNA Vaccine Sequences

| ORF (with JEV signal sequence underlined) | Protein (with JEV signal sequence underlined) |
|---|---|
| AUCCAGAUCAUGGACCUGGGCCACAUGUGC<br>GACGCCACCAUGAGCUACGAGUGCCCUAUG<br>CUGGACGAGGGCGUGGAGCCUGACGACGUG<br>GACUGCUGGUGCAACACCACCAGCACCUGG<br>GUGGUGUACGGCACCUGCCACCACAAGAAG<br>GGCGAGGCCAGAAGAAGCAGAAGAGCCGUG<br>ACCCUGCCUAGCCACAGCACCAGAAAGCUG<br>CAGACCAGAAGCCAGACCUGGCUGGAGAGC<br>AGAGAGUACACCAAGCACCUGAUCAGAGUG<br>GAGAACUGGAUCUUCAGAAACCCUGGCUUC<br>GCCCUGGCCGCCGCCGCCAUCGCCUGGCUG<br>CUGGGCAGCAGCACCAGCCAGAAGGUGAUC<br>UACCUGGUGAUGAUCCUGCUGAUCGCCCCU<br>GCCUACAGCAUCAGAUGCAUCGGCGUGAGC<br>AACAGAGACUUCGUGGAGGGCAUGAGCGGC<br>GGCACCUGGGUGGACGUGGUGCUGGAGCAC<br>GGCGGCUGCGUGACCGUGAUGGCCCAGGAC<br>AAGCCUGCCGUGGACAUCGAGCUGGUGACC<br>ACCACCGUGAGCAACAUGGCCGAGGUGAGA<br>AGCUACUGCUACGAGGCCAGCAUCAGCGAC<br>AUGGCCAGCGACAGCAGAUGCCCUAGAGAG<br>GGCGAGGCCUACCUGGACAAGCAGAGCGAC<br>ACCCAGUACGUGUGCAAGAGAACCCUGGUG<br>GACAGAGGCAGAGGCAACGGCUGCGGCAGA<br>UUCGGCAAGGGCAGCCUGGUGACCUGCGCC<br>AAGUUCGCCUGCAGCAAGAAGAUGACCGGC<br>AAGAGCAUCCAGCCUGAGAACCUGGAGUAC<br>AGAAUCAUGCUGAGCGUGCACGGCAGCCAG<br>CACAGCGGCAUGAUCGUGAACGACACCGGC<br>CACGAGACCGACGAGAACAGAGCCAAGGUG<br>GAGAUCACCCCUAACAGCCCUAGAGCCGAG<br>GCCACCCUGGGCGGCUUCGGCAGCCUGGGC<br>CUGGACUGCGAGCCUAGAACCGGCCUGGAC<br>UUCAGCGACCUGUACUACCUGACCAUGAAC<br>AACAAGCACUGGCUGGUGCACAAGGAGUGG<br>UUCCACGACAUCCCUCUGCCUUGGCACGCC<br>GGCGCCGACACCGGCACCCCUCACUGGAAC<br>AACAAGGAGGCCCUGGUGGAGUUCAAGGAC<br>GCCCACGCCAAGAGACAGACCGUGGUGGUG<br>CUGGGCAGCCAGGAGGGCGCCGUGCACACC<br>GCCCUGGCCGGCGCCCUGGAGGCCGAGAUG<br>GACGGCGCCAAGGGCAGACUGAGCAGCGGC<br>CACCUGAAGUGCAGACUGAAGAUGGACAAG<br>CUGAGACUGAAGGGCGUGAGCUACAGCCUG<br>UGCACCGCCGCCUUCACCUUCACCAAGAUC<br>CCUGCCGAGACCCUGCACGGCACCGUGACC<br>GUGGAGGUGCAGUACGCCGGCACCGACGGC<br>CCUUGCAAGGUGCCUGCCCAGAUGGCCGUG<br>GACAUGCAGACCCUGACCCCUGUGGGCAGA<br>CUGAUCACCGCCAACCCUGUGAUCACCGAG<br>AGCACCGAGAACAGCAAGAUGAUGCUGGAG<br>CUGGACCCUCCUUUCGGCGACAGCUACAUC<br>GUGAUCGGCGUGGGCGAGAAGAAGAUCACC<br>CACCACUGGCACAGAAGCGGCAGCACCAUC<br>GGCAAGGCCUUCGAGGCCACCGUGAGAGGC<br>GCCAAGAGAAUGGCCGUGCUGGGCGACACC<br>GCCUGGGACUUCGGCAGCGUGGGCGGCGCC<br>CUGAACAGCCUGGGCAAGGGCAUCCACCAG<br>AUCUUCGGCGCCGCCUUCAAGAGCCUGUUC<br>GGCGGCAUGAGCUGGUUCAGCCAGAUCCUG<br>AUCGGCACCCUGCUGGUGUGGCUGGGCCUG<br>AACACCAAGAACGGCAGCAUCAGCCUGACC<br>UGCCUGGCCCUGGGCGGCGUGCUGAUCUUC<br>CUGAGCACCGCCGUGAGCGCC (SEQ ID NO: 4) | WLLGSSTSQKVIYLVMILLIAPAYSIRCIGVSNR<br>DFVEGMSGGTWVDVVLEHGGCVTVMAQDKP<br>AVDIELVTTTVSNMAEVRSYCYEASISDMASD<br>SRCPREGEAYLDKQSDTQYVCKRTLVDRGRG<br>NGCGRFGKGSLVTCAKFACSKKMTGKSIQPEN<br>LEYRIMLSVHGSQHSGMIVNDTGHETDENRAK<br>VEITPNSPRAEATLGGFGSLGLDCEPRTGLDFS<br>DLYYLTMNNKHWLVHKEWFHDIPLPWHAGA<br>DTGTPHWNNKEALVEFKDAHAKRQTVVVLGS<br>QEGAVHTALAGALEAEMDGAKGRLSSGHLKC<br>RLKMDKLRLKGVSYSLCTAAFTFTKIPAETLH<br>GTVTVEVQYAGTDGPCKVPAQMAVDMQTLTP<br>VGRLITANPVITESTENSKMMLELDPPFGDSYI<br>VIGVGEKKITHHWHRSGSTIGKAFEATVRGAK<br>RMAVLGDTAWDFGSVGGALNSLGKGIHQIFG<br>AAFKSLFGGMSWFSQILIGTLLVWLGLNTKNG<br>SISLTCLALGGVLIFLSTAVSA (SEQ ID NO: 10) |
| ZIKV prME Africa Isolate (mRNA)<br>AUGUGGCUGGUGAGCCUGGCCAUCGUGACA<br>GCCUGCGCUGGAGCCGCCGAGAUCACCAGA<br>AGAGGCAGCGCCUACUACAUGUACCUGGAC<br>AGAAGCGACGCCGGCAAGGCCAUCAGCUUC<br>GCCACCACCCUGGGCGUGAACAAGUGCCAC<br>GUGCAGAUCAUGGACCUGGGCCACAUGUGC<br>GACGCCACCAUGAGCUACGAGUGCCCUAUG<br>CUGGACGAGGGCGUGGAGCCUGACGACGUG<br>GACUGCUGGUGCAACACCACCAGCACCUGG<br>GUGGUGUACGGCACCUGCCACCACAAGAAG | ZIKV prME Africa Isolate (protein)<br><u>MWLVSLAIVTACAGAAEITRRGSAYYMYLDR</u><br>SDAGKAISFATTLGVNKCHVQIMDLGHMCDA<br>TMSYECPMLDEGVEPDDVDCWCNTTSTWVVY<br>GTCHHKKGEARRSRRAVTLPSHSTRKLQTRSQ<br>TWLESREYTKHLIKVENWIFRNPGFALVAVAIA<br>WLLGSSTSQKVIYLVMILLIAPAYSIRCIGVSNR<br>DFVEGMSGGTWVDVVLEHGGCVTVMAQDKP<br>TVDIELVTTTVSNMAEVRSYCYEASISDMASDS<br>RCPTQGEAYLDKQSDTQYVCKRTLVDRGWGN<br>GCGLFGKGSLVTCAKFTCSKKMTGKSIQPENL |

TABLE 1-continued

ZIKV mRNA Vaccine Sequences

| ORF (with JEV signal sequence underlined) | Protein (with JEV signal sequence underlined) |
|---|---|
| GGCGAGGCCAGAAGAAGCAGACGUGCCGUG<br>ACCCUGCCUAGCCACAGCACCAGAAAGCUG<br>CAGACCAGAAGCCAGACCUGGCUGGAGAGC<br>AGAGAGUACACCAAGCACCUGAUCAAGGUG<br>GAGAACUGGAUCUUCAGAAACCCUGGCUUC<br>GCCCUGGUGGCCGUGGCAAUUGCCUGGCUG<br>CUGGGCAGCUCCACAAGCCAGAAGGUGAUC<br>UACCUGGUGAUGAUCCUGCUGAUCGCUCCA<br>GCCUACAGCAUCCGAUGCAUCGGCGUGAGC<br>AACAGAGACUUCGUGGAGGGCAUGAGCGGC<br>GGAACCUGGGUUGACGUGGUGCUGGAGCAC<br>GGCGGCUGCGUGACCGUGAUGGCCCAGGAC<br>AAGCCUACCGUGGACAUCGAGCUGGUGACC<br>ACCACCGUUAGCAACAUGGCCGAGGUGAGA<br>AGCUACUGCUACGAGGCAUCCAUCAGCGAC<br>AUGGCCAGCGACAGCCGCUGCCCUACCCAG<br>GGCAAGCAUACCUCGAUAAGCAGAGCGAC<br>ACCCAGUACGUGUGCAAGAGAACUCUCGUG<br>GACAGAGGCUGGGGCAACGGCUGCGGCCUG<br>UUCGGCAAGGGCAGCCUGGUGACUUGCGCC<br>AAGUUCACCUGCAGCAAGAAGAUGACCGGC<br>AAGAGCAUCCAGCCUGAGAACCUGGAGUAC<br>AGAAUCAUGCUGAGCGUGCACGGCAGCCAG<br>CACAGCGGCAUGAUCGGCUACGAAACUGAC<br>GAGGACAGAGCCAAGGUCGAAGUGACCCCU<br>AACAGCCCUAGAGCCGAGGCCACCCUUGGA<br>GGCUUCGGCUCCCUCGGCCUGGACUGCGAG<br>CCUAGAACAGGACUCGACUUCAGCGACCUG<br>UACUACCUGACCAUGAACAACAAGCACUGG<br>CUGGUCCACAAGGAGUGGUUCCACGACAUC<br>CCUCUGCCUUGGCACGCCGGAGCAGACACC<br>GGCACCCCUCACUGGAAUAACAAGGAGGCG<br>CUUGUGGAGUUCAAGGACGCCCACGCCAAG<br>AGACAGACCGUGGUUGUGCUCGGAAGUCAG<br>GAGGGCGCCGUGCACACCGCCCUGGCCGGA<br>GCCCUGGAGGCCGAGAUGGACGGCGCAAAG<br>GGCAGACUGUUCAGCGGCCACCUGAAGUGC<br>AGACUGAAGAUGGACAAGCUGAGACUUAAG<br>GGCGUCAGCUACAGCCUGUGCACCGCCGCC<br>UUCACCUUCACCAAGGUGCCUGCCGAAACC<br>CUGCACGGAACUGUAACCGUAGAGGUCCAG<br>UACCAGGAACCGACGGCCCUUGCAAGAUC<br>CCUGUGCAGAUGGCGGUGGAUAUGCAGACC<br>CUGACCCCUGUUGGCCGUUUGAUCACCGCC<br>AACCCUGUGAUAACCGAGAGCACCGAGAAC<br>AGCAAGAUGAUGCUGGAACUGGACCCUCCU<br>UUCGGCGACAGCUACAUCGUGAUCGGAGUG<br>GGCGAUAAGAAGAUCACCCACCACUGGCAU<br>CGCAGCGGUUCUACCAUCGGAAAGGCCUUC<br>GAAGCUACCGUUAGAGGUGCAAAGCGCAUG<br>GCAGUCUUAGGUGACACCGCCUGGGACUUC<br>GGUUCUGUCGGAGGCGUGUUCAACAGUCUG<br>GGCAAGGGAAUCCACCAGAUCUUCGGCGCU<br>GCCUUCAAGUCUUUGUUCGGAGGUAUGUCU<br>UGGUUCAGCCAGAUCCUGAUCGGCACCCUU<br>CUGGUUUGGCUGGGCCUCAACACCAAGAAC<br>GGAUCCAUAUCCCUGACCUGCUGGCCUUG<br>GGCGGUGUCAUGAUCUUCCUGUCGACUGCC<br>GUGAGCGCC (SEQ ID NO: 5) | EYRIMLSVHGSQHSGMIGYETDEDRAKVEVTP<br>NSPRAEATLGGFGSLGLDCEPRTGLDFSDLYYL<br>TMNNKHWLVHKEWFHDIPLPWHAGADTGTP<br>HWNNKEALVEFKDAHAKRQTVVVLGSQEGA<br>VHTALAGALEAEMDGAKGRLFSGHLKCRLKM<br>DKLRLKGVSYSLCTAAFTFTKVPAETLHGTVT<br>VEVQYAGTDGPCKIPVQMAVDMQTLTPVGRLI<br>TANPVITESTENSKMMLELDPPFGDSYIVIGVG<br>DKKITHHWHRSGSTIGKAFEATVRGAKRMAV<br>LGDTAWDFGSVGGVFNSLGKGIHQIFGAAFKS<br>LFGGMSWFSQILIGTLLVWLGLNTKNGSISLTC<br>LALGGVMIFLSTAVSA (SEQ ID NO: 11) |
| ZIKV prME Africa Isolate (mRNA), with<br>T76R, Q77E, W101R, L107R mutations<br>AUGUGGCUGGUGAGCCUGGCCAUCGUGACU<br>GCUUGCGCGGGUGCCGCCGAGAUCACCAGA<br>AGAGGCAGCGCCUACUACAUGUACCUGGAC<br>AGAAGCGACGCCGGCAAGGCCAUCAGCUUC<br>GCCACCACCCUGGGCGUGAACAAGUGCCAC<br>GUGCAGAUCAUGGACCUGGGCCACAUGUGC<br>GACGCCACCAUGAGCUACGAGUGCCCUAUG<br>CUGGACGAGGGCGUGGAGCCUGACGACGUG<br>GACGUGUGCUGGAACACCACCAGCACCUGG<br>GUGGUGUACGGCACCUGCCACCACAAGAAG<br>GGCGAGGCCAGAAGAAGCAGGAGGGCCGUG<br>ACCCUGCCUAGCCACAGCACCAGAAAGCUG<br>CAGACCAGAAGCCAGACCUGGCUGGAGAGC<br>AGAGAGUACACCAAGCACCUGAUCAAGGUG | ZIKV prME Africa Isolate (protein), with<br>T76R, Q77E, W101R, L107R mutations<br>MWLVSLAIVTACAGAAEITRRGSAYYMYLDR<br>SDAGKAISFATTLGVNKCHVQIMDLGHMCDA<br>TMSYECPMLDEGVEPDDVDCWCNTTSTWVVY<br>GTCHHKKGEARRSRRAVTLPSHSTRKLQTRSQ<br>TWLESREYTKHLIKVENWIFRNPGFALVAVAIA<br>WLLGSSTSQKVIYLVMILLIAPAYSIRCIGVSNR<br>DFVEGMSGGTWVDVVLEHGGCVTVMAQDKP<br>TVDIELVTTTVSNMAEVRSYCYEASISDMASDS<br>RCPREGEAYLDKQSDTQYVCKRTLVDRGRGN<br>GCGRFGKGSLVTCAKFTCSKKMTGKSIQPENL<br>EYRIMLSVHGSQHSGMIGYETDEDRAKVEVTP<br>NSPRAEATLGGFGSLGLDCEPRTGLDFSDLYYL<br>TMNNKHWLVHKEWFHDIPLPWHAGADTGTP<br>HWNNKEALVEFKDAHAKRQTVVVLGSQEGA |

TABLE 1-continued

ZIKV mRNA Vaccine Sequences

| ORF (with JEV signal sequence underlined) | Protein (with JEV signal sequence underlined) |
|---|---|
| GAGAACUGGAUCUUCAGAAACCCUGGCUUC<br>GCCCUGGUGGCCGUGGCUAUAGCCUGGCUG<br>CUGGGAUCUUCAACAAGCCAGAAGGUGAUC<br>UACCUGGUGAUGAUCCUGCUGAUCGCGCCA<br>GCCUACAGCAUCCGCUGCAUCGGCGUGAGC<br>AACAGAGACUUCGUGGAGGGCAUGAGCGGC<br>GGAACUUGGGUGGACGUGGUGCUGGAGCAC<br>GGCGGCUGCGUGACCGUGAUGGCCCAGGAC<br>AAGCCUACCGUGGACAUCGAGCUGGUGACC<br>ACCACGGUUUCUAAUAUGGCCGAGGUGAGA<br>AGCUACUGCUACGAGGCAUCCAUCAGCGAC<br>AUGGCCAGCGACAGCAGGUGCCCUAGAGAA<br>GGAGAAGCCUAUCUCGACAAGCAGAGCGAC<br>ACCCAGUACGUGUGCAAGAGAACCCUCGUG<br>GACAGAGGCAGAGGCAACGGCUGCGGCAGA<br>UUCGGCAAGGGCAGCCUGGUUACGUGCGCC<br>AAGUUCACCUGCAGCAAGAAGAUGACCGGC<br>AAGAGCAUCCAGCCUGAGAACCUGGAGUAC<br>AGAAUCAUGCUGAGCGUGCACGGCAGCCAG<br>CACAGCGGCAUGAUCGGCUACGAGACAGAC<br>GAGGACAGAGCUAAGGUCGAGGUGACCCCU<br>AACUCCCCACGCGCCGAGGCUACGCUGGGA<br>GGCUUCGGAUCUCUGGGCCUGGACUGCGAG<br>CCUAGAACCGGCUUGGAUUUCAGCGACCUG<br>UACUACCUGACCAUGAACAACAAGCACUGG<br>UUGGUCCACAAGGAGUGGUUCCACGACAUC<br>CCUCUGCCUUGGCACGCGGGCGCUGACACC<br>GGCACCCCUCACUGGAAUAACAAGGAGGCC<br>UUGGUGGAGUUCAAGGACGCCCACGCCAAG<br>AGACAGACCGUGGUGGUCUUGGGUUCCCAG<br>GAGGGCGCCGUGCACACCGCCCUGGCAGGA<br>GCUCUGGAGGCCGAGAUGGACGGCGCCAAG<br>GGUAGACUGUUCAGCGGCCACCUGAAGUGC<br>AGACUGAAGAUGGAUAAGCUGAGACUCAAG<br>GGUGUGUCAUACAGCCUGUGCACCGCCGCC<br>UUCACCUUCACCAAGGUGCCUGCCGAAACC<br>CUGCACGGAACCGUGACUGUAGAGGUACAG<br>UACGCUGGCACCGACGGCCCUUGCAAGAUC<br>CCUGUGCAGAUGGCCGUUGACAUGCAGACC<br>CUGACCCCUGUGGGCAGGCUGAUCACCGCC<br>AACCCUGUGAUCACUGAGAGCACCGAGAAC<br>AGCAAGAUGAUGCUGGAACUGGACCCUCCU<br>UUCGGCGACAGCUACAUCGUGAUAGGCGUG<br>GGCGAUAAGAAGAUCACCCACCAUUGGCAC<br>AGAAGUGGUUCGACUAUCGGUAAGGCAUUC<br>GAAGCUACAGUGAGAGGAGCCAAGAGGAUG<br>GCAGUGCUGGGUGACACCGCCUGGGAUUUC<br>GGUUCAGUGGGCGGCGUGUUCAAUUCCCUG<br>GGCAAGGGUAUCCACCAGAUCUUCGGCGCU<br>GCCUUCAAGAGCCUGUUCGGUGGAAUGAGC<br>UGGUUCAGCCAGAUCCUGAUCGGCACCCUC<br>CUGGUUUGGCUUGGUUUGAACACCAAGAAC<br>GGCUCUAUUUCCCUGACCUGCCUGGCACUA<br>GGAGGCGUCAUGAUAUUCCUGAGUACCGCC<br>GUGAGCGCC (SEQ ID NO: 6) | VHTALAGALEAEMDGAKGRLFSGHLKCRLKM<br>DKLRLKGVSYSLCTAAFTFTKVPAETLHGTVT<br>VEVQYAGTDGPCKIPVQMAVDMQTLTPVGRLI<br>TANPVITESTENSKMMLELDPPFGDSYIVIGVG<br>DKKITHHWHRSGSTIGKAFEATVRGAKRMAV<br>LGDTAWDFGSVGGVFNSLGKGIHQIFGAAFKS<br>LFGGMSWFSQILIGTLLVWLGLNTKNGSISLTC<br>LALGGVMIFLSTAVSA (SEQ ID NO: 12) |

Any of the open reading frames (ORFs) provided in Table 1 may include any of the following 5' UTR sequences or other 5' UTR sequence (e.g., wild-type 5' UTR sequence):

(SEQ ID NO: 13)
GGGAAAUAAGAGAGAAAAGAAGAGUAAGAAGAAAUAUAAGACCCCGGCG
CCGCCACC

(SEQ ID NO: 14)
GGGAAAUAAGAGAGAAAAGAAGAGUAAGAAGAAAUAUAAGAGCCACC.

Likewise, any of the ORFs provided in Table 1 may include any of the following 3' UTR sequences or other 3' UTR sequence (e.g., wild-type 3' UTR sequence):

(SEQ ID NO: 15)
UGAUAAUAGGCUGGAGCCUCGGUGGCCUAGCUUCUUGCCCCUUGGGCCUC
CCCCCAGCCCCUCCUCCCCUUCCUGCACCCGUACCCCGUGGUCUUUGAA
UAAAGUCUGAGUGGGCGGC (SEQ ID NO: 16)
UGAUAAUAGGCUGGAGCCUCGGUGGCCAUGCUUCUUGCCCCUUGGGCCUC
CCCCCAGCCCCUCCUCCCCUUCCUGCACCCGUACCCCGUGGUCUUUGAA
UAAAGUCUGAGUGGGCGGC

Further, any of the ORFs provided in Table 1 may include a polyA tail (e.g., 100 nucleotides).

In some embodiments, a ZIKV mRNA vaccine (mRNA-1893) comprises the following sequence, including a 5' UTR, 3' UTR and polyA tail:

(SEQ ID NO: 20)
GGGAAAUAAGAGAGAAAAGAAGAGUAAGAAGAAAUAUAAGACCCCGGCGC

CGCCACCAUGUGGCUGGUGUCCCUGGCCAUCGUGACAGCCUGUGCUGGCG

CCGCUGAAGUGACCAGAAGAGGCAGCGCCUACUACAUGUACCUGGACCGG

AACGAUGCCGGCGAGGCCAUCAGCUUUCCAACCACCCUGGGCAUGAACAA

GUGCUACAUCCAGAUCAUGGACCUGGGCCACAUGUGCGACGCCACCAUGA

GCUACGAGUGCCCCAUGCUGGACGAGGGCGUGGAACCCGACGAUGUGGAC

UGCUGGUGCAACACCACCAGCACCUGGGUGGUGUACGGCACCUGUCACCA

CAAGAAGGGCGAAGCCAGACGGUCCAGACGGGCCGUGACACUGCCUAGCC

ACAGCACCAGAAAGCUGCAGACCCGGUCCCAGACCUGGCUGGAAAGCAGA

GAGUACACCAAGCACCUGAUCCGGGUGGAAAACUGGAUCUUCCGGAACCC

CGGCUUUGCCCUGGCCGCUGCUGCUAUUGCUUGGCUGCUGGGCAGCAGCA

CCUCCCAGAAAGUGAUCUACCUCGUGAUGAUCCUGCUGAUCGCCCCUGCC

UACAGCAUCCGGUGUAUCGGCGUGUCCAACCGGGACUUCGUGGAAGGCAU

GAGCGGCGGCACAUGGGUGGACGUGGUGCUGGAACAUGGCGGCUGCGUGA

CAGUGAUGGCCCAGGACAAGCCCACCGUGGACAUCGAGCUCGUGACCACC

ACCGUGUCCAAUAUGGCCGAAGUGCGGAGCUACUGCUACGAGGCCAGCAU

CAGCGACAUGGCCAGCGACAGCAGAUGCCCUACACAGGGCGAGGCCUACC

UGGACAAGCAGUCCGACACCCAGUACGUGUGCAAGCGGACCCUGGUGGAU

AGAGGCUGGGGCAAUGGCUGCGGCCUGUUUGGCAAGGGCAGCCUCGUGAC

CUGCGCCAAGUUCGCCUGCAGCAAGAAGAUGACCGGCAAGAGCAUCCAGC

CCGAGAACCUGGAAUACCGGAUCAUGCUGAGCGUGCACGGCAGCCAGCAC

UCCGGCAUGAUCGUGAACGACACCGGCCACGAGACAGACGAGAACCGGGC

CAAGGUGGAAAUCACCCCUAACAGCCCUAGAGCCGAGGCCACACUGGGCG

GCUUUGGAUCUCUGGGCCUGGACUGCGAGCCUAGAACCGGCCUGGAUUUC

AGCGACCUGUACUACCUGACCAUGAACAACAAGCACUGGCUGGUGCACAA

AGAGUGGUUCCACGACAUCCCUCUGCCCUGGCAUGCCGGCGCUGAUACAG

GCACACCCCACUGGAACAACAAAGAGGCUCUGGUGGAAUUCAAGGACGCC

CACGCCAAGCGGCAGACCGUGGUGGUGCUGGGAUCUCAGGAAGGCGCCGU

GCAUACAGCUCUGGCAGGCGCCCUGGAAGCCGAAAUGGAUGGCGCCAAAG

GCAGACUGUCCAGCGGCCACCUGAAGUGCCGGCUGAAGAUGGACAAGCUG

CGGCUGAAGGGCGUGUCCUACUCCCUGUGUACCGCCGCCUUCACCUUCAC

CAAGAUCCCCGCCGAGACACUGCACGGCACCGUGACUGUGGAAGUGCAGU

ACGCCGGCACCGACGGCCCUUGUAAAGUGCCUGCUCAGAUGGCCGUGGAU

AUGCAGACCCUGACCCCUGUGGGCAGACUGAUCACCGCCAACCCCGUGAU

CACCGAGAGCACCGAGAACAGCAAGAUGAUGCUGGAACUGGACCCACCCU

UCGGCGACAGCUACAUCGUGAUCGGCGUGGAGAAGAAGAUCACCCAC

CACUGGCACAGAAGCGGCAGCACCAUCGGCAAGGCCUUUGAGGCUACAGU

GCGGGGAGCCAAGAGAAUGGCCGUGCUGGGAGAUACCGCCUGGGACUUUG

GCUCUGUGGGCGGAGCCCUGAACUCUCUGGGCAAGGGAAUCCACCAGAUC

UUCGGAGCCGCCUUUAAGAGCCUGUUCGGCGGCAUGAGCUGGUUCAGCCA

GAUCCUGAUCGGCACCCUGCUGAUGUGGCUGGGCCUGAACACCAAGAACG

GCAGCAUCUCCCUGAUGUGCCUGGCUCUGGGGAGGCGUGCUGAUCUUCCUG

AGCACAGCCGUGUCUGCCUGAUAAUAGGCUGGAGCCUCGGUGGCCUAGCU

UCUUGCCCCUUGGGCCUCCCCCCAGCCCCUCCUCCCCUUCCUGCACCCGU

ACCCCCGUGGUCUUUGAAUAAAGUCUGAGUGGGCGGCAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAA

Examples

Figure 2:
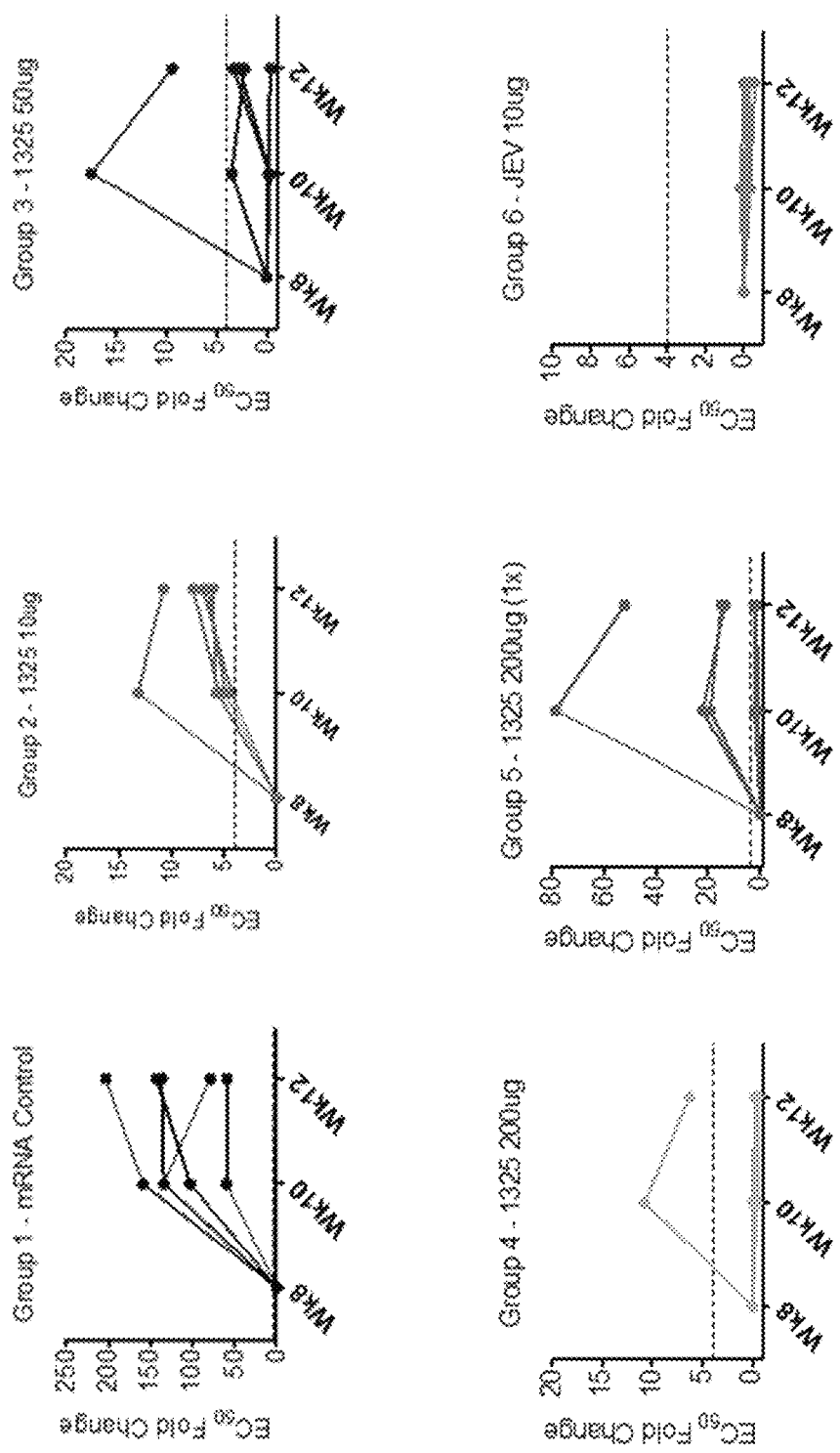
FIG. 2 includes graphs showing neutralizing antibody titers ($EC_{50}$ fold change relative to week 8) obtained from the same NHP experiments described in FIG. 1.

Non-human primates (n=5) were immunized intramuscularly (IM) with a vaccine composition comprising mRNA encoding either an IgE signal peptide fused to a ZIKV prME antigen (mRNA-1325, SEQ ID NO:17) (a single 200 μg dose, or a 10 μg, 50 μg or 200 μg dose followed by an equivalent boost at week 4, or a JEV signal peptide fused to a ZIKV prME antigen (mRNA-1893, SEQ ID NO:7) (a 10 μg followed by an equivalent boost at week 4). Animals were challenged at week 8 with 1000 focus-forming units (FFU) of Zika virus. Serum was collected 3, 4, 5, 6 and 7 days post challenge. The data in FIG. 1 shows that while a single 200 μg dose of the mRNA-1325 vaccine conferred nearly complete protection, the mRNA-1893 vaccine unexpectedly provided sterilizing immunity at a 20 fold lower dose. Neutralizing antibody titers ($EC_{50}$ fold change relative to week 8) are shown in FIG. 2.

mRNA-1325

(SEQ ID NO: 17)
MDWTWILFLVAAATRVHSVEVTRRGSAYYMYLDRSDAGEAISFPTTLGM

NKCYIQIMDLGHMCDATMSYECPMLDEGVEPDDVDCWCNTTSTWVVYGT

CHHKKGEARRSRRAVTLPSHSTRKLQTRSQTWLESREYTKHLIRVENWI

FRNPGFALAAAAIAWLLGSSTSQKVIYLVMILLIAPAYSIRCIGVSNRD

FVEGMSGGTWVDVVLEHGGCVTVMAQDKPAVDIELVTTTVSNMAEVRSY

CYEASISDMASDSRCPTQGEAYLDKQSDTQYVCKRTLVDRGWGNGCGLF

GKGSLVTCAKFACSKKMTGKSIQPENLEYRIMLSVHGSQHSGMIVNDTG

HETDENRAKVEITPNSPRAEATLGGFGSLGLDCEPRTGLDFSDLYYLTM

NNKHWLVHKEWFHDIPLPWHAGADTGTPHWNNKEALVEFKDAHAKRQTV

VVLGSQEGAVHTALAGALEAEMDGAKGRLSSGHLKCRLKMDKLRLKGVS

YSLCTAAFTFTKIPAETLHGTVTVEVQYAGTDGPCKVPAQMAVDMQTLT

PVGRLITANPVITESTENSKMMLELDPPFGDSYIVIGVGEKKITHHWHR

SGSTIGKAFEATVRGAKRMAVLGDTAWDFGSVGGALNSLGKGIHQIFGA

AFKSLFGGMSWFSQILIGTLLVWLGLNTKNGSISLTCLALGGVLIFLST

AVSA mRNA-1893

(SEQ ID NO: 7)
MWLVSLAIVTACAGAAEVTRRGSAYYMYLDRNDAGEAISFPTTLGMNKCY

IQIMDLGHMCDATMSYECPMLDEGVEPDDVDCWCNTTSTWVVYGTCHHKK

-continued

GEARRSRRAVTLPSHSTRKLQTRSQTWLESREYTKHLIRVENWIFRNPGF

ALAAAAIAWLLGSSTSQKVIYLVMILLIAPAYSIRCIGVSNRDFVEGMSG

GTWVDVVLEHGGCVTVMAQDKPTVDIELVTTTVSNMAEVRSYCYEASISD

MASDSRCPTQGEAYLDKQSDTQYVCKRTLVDRGWGNGCGLFGKGSLVTCA

KFACSKKMTGKSIQPENLEYRIMLSVHGSQHSGMIVNDTGHETDENRAKV

EITPNSPRAEATLGGFGSLGLDCEPRTGLDFSDLYYLTMNNKHWLVHKEW

FHDIPLPWHAGADTGTPHWNNKEALVEFKDAHAKRQTVVVLGSQEGAVHT

ALAGALEAEMDGAKGRLSSGHLKCRLKMDKLRLKGVSYSLCTAAFTFTKI

PAETLHGTVTVEVQYAGTDGPCKVPAQMAVDMQTLTPVGRLITANPVITE

STENSKMMLELDPPFGDSYIVIGVGEKKITHHWHRSGSTIGKAFEATVRG

AKRMAVLGDTAWDFGSVGGALNSLGKGIHQIFGAAFKSLFGGMSWFSQIL

IGTLLMWLGLNTKNGSISLMCLALGGVLIFLSTAVSA

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising administering to a subject an immunogenic composition comprising a messenger ribonucleic acid (mRNA) that comprises an open reading frame (ORF) encoding a JEV signal peptide fused to a Zika virus (ZIKV) prME protein formulated in a lipid nanoparticle in an effective amount to induce in the subject a ZIKV prME-specific immune response, wherein the ORF comprises the sequence of SEQ ID NO: 1.

2. The method of claim 1, wherein the effective amount reduces viral load in the subject by at least 80%, relative to a control, at 3-7 days following exposure to ZIKV, wherein the control is the viral load in a subject administered a ZIKV RNA vaccine lacking the JEV signal sequence.

3. The method of claim 1, wherein the effective amount is sufficient to produce detectable levels of ZIKV prME protein as measured in serum of the subject at 1-72 hours post administration.

4. The method of claim 1, wherein the effective amount is a total dose of 20 µg-200 µg.

5. The method of claim 1, wherein the mRNA comprises the sequence of SEQ ID NO:20.

6. The method of claim 1, wherein the immunogenic composition further comprises a 5' untranslated region (UTR) comprising a sequence selected from SEQ ID NO:13 and SEQ ID NO:14.

7. The method of claim 1, wherein the immunogenic composition further comprises a 3' UTR comprising a sequence selected from SEQ ID NO:15 and SEQ ID NO:16.

8. The method of claim 1, wherein the immunogenic composition comprises at least one modified nucleotide.

9. The method of claim 1, wherein at least 80% of uracil nucleotides in the ORF have a chemical modification selected from N1-methyl-pseudouridine or N1-ethyl-pseudouridine.

10. The method of claim 1, wherein the lipid nanoparticle comprises a molar ratio of 20-60% ionizable cationic lipid, 5-25% non-cationic lipid, 25-55% sterol, and 0.5-15% PEG-modified lipid.

11. The method of claim 10, wherein the ionizable cationic lipid comprises the following compound:

[chemical structure]

12. A method comprising administering to a subject an immunogenic composition comprising a messenger ribonucleic acid (mRNA) that comprises a 5' UTR, an open reading frame (ORF) encoding a JEV signal peptide fused to a Zika virus (ZIKV) prME protein, and a 3' UTR formulated in a lipid nanoparticle in an effective amount to induce in the subject a ZIKV prME-specific immune response, wherein the JEV signal peptide comprises the sequence of SEQ ID NO:18, the 5' UTR comprises the sequence of SEQ ID NO:13, and the 3'UTR comprises the sequence of SEQ ID NO:15.

13. The method of claim 12, wherein the effective amount reduces viral load in the subject by at least 80%, relative to a control, at 3-7 days following exposure to ZIKV, wherein the control is the viral load in a subject administered a ZIKV RNA vaccine lacking the JEV signal sequence.

14. The method of claim 12, wherein the effective amount is sufficient to produce detectable levels of ZIKV prME protein as measured in serum of the subject at 1-72 hours post administration.

15. The method of claim 12, wherein the effective amount is a total dose of 20 µg-200 µg.

16. The method of claim 12, wherein the immunogenic composition comprises at least one modified nucleotide.

17. The method of claim 1, wherein at least 80% of uracil nucleotides in the ORF have a chemical modification selected from N1-methyl-pseudouridine or N1-ethyl-pseudouridine.

18. The method of claim 12, wherein the lipid nanoparticle comprises a molar ratio of 20-60% ionizable cationic lipid, 5-25% non-cationic lipid, 25-55% sterol, and 0.5-15% PEG-modified lipid.

19. The method of claim 18, wherein the ionizable cationic lipid comprises the following compound:

[chemical structure]

* * * * *

SEQUENCE LISTING

<160> NUMBER OF SEQ ID NOS: 20

<210> SEQ ID NO 1
<211> LENGTH: 2061
<212> TYPE: RNA
<213> ORGANISM: Artificial Sequence
<220> FEATURE:
<223> OTHER INFORMATION: Synthetic Polynucleotide

<400> SEQUENCE: 1

| | | | | | | |
|---|---|---|---|---|---|---|
| auggcugg | uguccuggc | caucgugaca | gccugugcug | gcgccgcuga | agugaccaga | 60 |
| agaggcagcg | ccuacuacau | guaccuggac | cggaacgaug | ccggcgaggc | caucagcuuu | 120 |
| ccaaccaccc | ugggcaugaa | caagugcuac | auccagauca | uggaccuggg | ccacaugugc | 180 |
| gacgccacca | ugagcuacga | gugccccaug | cuggacgagg | gcguggaacc | cgacgaugug | 240 |
| gacugcuggu | gcaacaccac | cagcaccugg | gugguguacg | gcaccuguca | ccacaagaag | 300 |
| ggcgaagcca | gacgguccag | acgggccgug | acacugccua | gccacagcac | cagaaagcug | 360 |
| cagacccggu | cccagaccug | gcuggaaagc | agagaguaca | ccaagcaccu | gauccgggug | 420 |
| gaaaacugga | ucuuccggaa | ccccggcuuu | gcccuggccg | cugcugcuau | ugcuuggcug | 480 |
| cugggcagca | gcaccuccca | gaaagugauc | uaccucguga | ugauccugcu | gaucgcccu | 540 |
| gccuacagca | uccggugau | cggcguguc | aaccgggacu | ucguggaagg | caugagcggc | 600 |
| ggcacauggg | uggacguggu | gcuggaacau | ggcggcugcg | ugacagugau | ggcccaggac | 660 |
| aagcccaccg | uggacaucga | gcucgugacc | accaccgugu | ccaauauggc | cgaagugcgg | 720 |
| agcuacugcu | acgaggccag | caucagcgac | auggccagcg | acagcagaug | cccuacacag | 780 |
| ggcgaggccu | accuggacaa | gcaguccgac | acccaguacg | ugugcaagcg | gacccuggug | 840 |
| gauagaggcu | ggggcaaugg | cugcggccug | uuuggcaagg | gcagccucgu | gaccugcgcc | 900 |
| aaguucgcca | gcagcaagaa | gaugaccggc | aagagcaucc | agcccgagaa | ccuggaauac | 960 |
| cggaucaugc | ugagcgugca | cggcagccag | cacuccggca | ugaucgugaa | cgacaccggc | 1020 |
| cacgagacag | acgagaaccg | ggccaaggug | gaaaucaccc | cuaacagccc | uagagccgag | 1080 |
| gccacacugg | gcggcuuugg | aucucugggc | cuggacugcg | agccuagaac | cggccuggau | 1140 |
| uucagcgacc | uguacuaccu | gaccaugaac | aacaagcacu | ggcugguca | caaagagugg | 1200 |

| | |
|---|---|
| uuccacgaca ucccucugcc cuggcaugcc ggcgcugaua caggcacacc ccacuggaac | 1260 |
| aacaaagagg cucuggugga auucaaggac gcccacgcca agcggcagac cgugguggug | 1320 |
| cugggaucuc aggaaggcgc cgugcauaca gcucuggcag gcgcccugga agccgaaaug | 1380 |
| gauggcgcca aaggcagacu guccagcggc caccugaagu gccggcugaa gauggacaag | 1440 |
| cugcggcuga agggcguguc cuacucccug uguaccgccg ccuucaccuu caccaagauc | 1500 |
| cccgccgaga cacugcacgg caccgugacu guggaagugc aguacgccgg caccgacggc | 1560 |
| ccuuguaaag ugccugcuca gauggccgug gauaugcaga cccugacccc ugugggcaga | 1620 |
| cugaucaccg ccaaccccgu gaucaccgag agcaccgaga cagcaagau gaugcuggaa | 1680 |
| cuggacccac ccuucggcga cagcuacauc gugaucggcg ugggagagaa gaagaucacc | 1740 |
| caccacuggc acagaagcgg cagcaccauc ggcaaggccu uugaggcuac agugcgggga | 1800 |
| gccaagagaa uggccgugcu gggagauacc gccugggacu uggcucugu gggcggagcc | 1860 |
| cugaacucuc ugggcaaggg aauccaccag aucuucggag ccgccuuuaa gagccuguuc | 1920 |
| ggcggcauga gcugguucag ccagauccug aucggcaccc ugcugaugug gcugggccug | 1980 |
| aacaccaaga acggcagcau cucccugaug gccuggcuc ugggaggcgu gcugaucuuc | 2040 |
| cugagcacag ccgugucugc c | 2061 |

<210> SEQ ID NO 2
<211> LENGTH: 2061
<212> TYPE: RNA
<213> ORGANISM: Artificial Sequence
<220> FEATURE:
<223> OTHER INFORMATION: Synthetic Polynucleotide

<400> SEQUENCE: 2

| | |
|---|---|
| auguggcugg ugucccuggc caucgugaca gccugugcug gcgccgcuga agugaccaga | 60 |
| agaggcagcg ccuacuacau guaccuggac cggaacgaug ccggcgaggc caucagcuuu | 120 |
| ccaaccaccc ugggcaugaa caagugcuac auccagauca uggaccuggg ccacaugugc | 180 |
| gacgccacca ugagcuacga gugccccaug cuggacgagg gcguggaacc cgacgaugug | 240 |
| gacugcuggu gcaacaccac cagcaccugg guggugacg gcaccuguca ccacaagaag | 300 |
| ggcgaagcca gacgguccag acgggccgug acacugccua gccacagcac cagaaagcug | 360 |
| cagacccggu cccagaccug gcuggaaagc agagaguaca ccaagcaccu gauccggguc | 420 |
| gaaaacugga ucuuccggaa ccccggcuuu gcccuggccg cugcugcuau ugcuuggcug | 480 |
| cugggcagca gcaccuccca gaaagugauc uaccucguga ugauccugcu gaucgccccu | 540 |
| gccuacagca uccggguguau cggcgugucc aacggggacu ucguggaagg caugagcggc | 600 |
| ggcacauggg uggacuggu gcuggaacau ggcggcugcg ugacagugau ggcccaggac | 660 |
| aagcccaccg uggacaucga gcucgugacc accaccgugu ccaauauggc cgaagugcgg | 720 |
| agcuacugcu acgaggccag caucagcgac auggccagcg acagcagaug ccccagagag | 780 |
| ggcgaggccu accuggacaa gcaguccgac acccaguacg ugugcaagcg gacccuggug | 840 |
| gacagaggca gaggcaaugg cugcggcaga uucggcaagg gcagccucgu gaccugcgcc | 900 |
| aaguucgccu gcagcaagaa gaugaccggc aagagcaucc agcccgagaa ccuggaauac | 960 |
| cggaucaugc ugagcgugca cggcagccag cacuccggca ugaucgugaa cgacaccggc | 1020 |
| cacgagacag acgagaaccg ggccaaggug gaaaucaccc cuaacagccc uagagccgag | 1080 |
| gccacacugg gcgguuugg aucucugggc cuggacgcga gccuagaac cggccuggau | 1140 |

```
uucagcgacc uguacuaccu gaccaugaac aacaagcacu ggcuggugca caaagagugg     1200
uuccacgaca ucccucugcc cuggcaugcc ggcgcugaua caggcacacc ccacuggaac     1260
aacaaagagg cucuggugga auucaaggac gcccacgcca agcggcagac cguggugug     1320 cugggaucuc aggaaggcgc cgugcauaca gcucuggcag gcgcccugga agccgaaaug     1380 gaugcgcca aaggcagacu guccagcggc caccugaagu gccggcugaa gauggacaag     1440
cugcggcuga agggcguguc cuacucccug uguaccgccg ccuucaccuu caccaagauc     1500
cccgccgaga cacugcacgg caccgugacu guggaagugc aguacgccgg caccgacggc     1560
ccuuguaaag ugccugcuca gauggccgug gauaugcaga cccugacccc uguggggcaga     1620 cugaucaccg ccaaccccgu gaucaccgag agcaccgaga acagcaagau gaugcuggaa     1680
cuggacccac ccuucggcga cagcuacauc gugaucggcg ugggagagaa gaagaucacc     1740
caccacuggc acagaagcgg cagccaucau ggcaaggccu uugaggcuac agugcgggga     1800
gccaagagaa uggccgugcu gggagauacc gccuggacu uggcucugu gggcggagcc      1860 cugaacucuc uggcaagggg aauccaccag aucuucggag ccgccuuuaa gagccuguuc     1920
ggcggcauga gcugguucag ccagauccug aucggcaccc ugcugaugug gcugggccug     1980
aacaccaaga acggcagcau cucccugaug gccuggcuc ugggaggcgu gcugaucuuc      2040
cugagcacag ccgugucugc c                                                2061
```

<210> SEQ ID NO 3
<211> LENGTH: 2061
<212> TYPE: RNA
<213> ORGANISM: Artificial Sequence
<220> FEATURE:
<223> OTHER INFORMATION: Synthetic Polynucleotide
<400> SEQUENCE: 3

```
auguggcugg ugagccuggc caucgugacc gccugcgccg gcgccgugga ggugaccaga       60
agaggcagcg ccuacuacau guaccuggac agaagcgacg ccggcgaggc caucagcuuc      120
ccuaccaccc ugggcaugaa caagugcuac auccagauca uggaccuggg ccacaugugc      180
gacgccacca ugagcuacga gugcccuaug cuggacgagg gcguggagcc ugacgacgug      240
gacugcuggu gcaacaccac cagcaccugg guggguacg gcaccugcca ccacaagaag      300
ggagaggcga gaagaagcag gagagccgug acccugccua gccacagcac cagaaagcug      360
cagacccgga gccagaccug gcuggagagc agagaguaca ccaagcaccu gaucagagug      420
gagaacugga ucuucagaaa cccuggcuuc gcccuggccg cggcugcuau cgccuggcug      480
cuggguaguu caaccagcca gaaggugauc uaccuuguga ugauccugcu gaucgccccg     540
gcauacagca uccgcugcau cggcgugagc aacagagacu ucguggaggg caugagcgga      600
ggaacguggg uugacguggu gcuggagcac ggcggcucgc ugaccgugau ggcccaggac      660
aagccugccg uggacaucga gcuggugacc accaccguau ccaacauggc cgaggugaga      720
agcuacugcu acgaggcuag cauaagcgac auggccagc acagccgaug cccuacccag      780
ggagaagccu accuggacaa gcagagcgac acccaguacg ugugcaagag aacccuggug      840
gacagaggcu ggggcaacgg cugcggccug uucggcaagg gcagccuggu acuugcgcc      900 aaguucgccu gcagcaagaa gaugaccggc aagagcaucc agccugagaa ccuggaguac      960
agaaucaugc ugagcguggc aggcagccag cacagcggca ugaucgugaa cgacaccggc     1020
cacgaaacag acgagaacag agccaaggug gagaucaccc cuaacagccc uagagccgag     1080
gccacccuug gcggcuucgg cagccucggc cuggacugcg agccuagaac gggccuggau     1140
```

```
uucagcgacc uguacuaccu gacuaugaau aacaagcacu ggcuuguuca caaggagugg   1200
uuccacgaca ucccucugcc uuggcacgcg ggagcugaca caggaacccc ucacuggaac   1260
aacaaggagg cccuaguuga guucaaggac gcccacgcca agagacagac cguggucgug   1320 cugguuccc aagagggcgc uguccacacu gcacucgcug gcgcccugga ggccgagaug    1380
gacggcgcca agggaagacu gagcagcggc caccugaagu gcaggcugaa gauggacaag   1440
cugcggcuga agggcguguc cuacagccug ugcaccgccg ccuucaccuu caccaagauc   1500
ccugccgaga cacuacacgg cacagugacc gucgaggugc aguacgccgg caccgacggc   1560
ccuugcaagg ugccugccca gauggccguc gauaugcaaa cucugacccc ugugggacgg   1620
cuuaucaccg ccaacccugu gauuacugag agcaccgaga auagcaagau gauguuggaa   1680
cuggacccuc cuuucggcga cagcuacauc gugauuggga uuggagagaa gaagaucaca   1740
caccacuggc acagaucugg aucuacuauu ggcaaggccu ucgaggcaac agugagagga   1800
gcaaagagaa uggcaguucu gggagacacc gccuggauu ucggaagcgu aggaggugca    1860
uugaacuccc uaggaaaggg aauccaccag aucuucggag cugcauucaa gagccuauuc   1920
ggcggaaugu ccugguucag ccagauccug aucggcaccc ugcuugugug gcuuggauug   1980
aacaccaaga acggaaguau uagucugacc ugccuggcuc ucggcggugu gcugaucuuc   2040
cugaguacug cggugagcgc c                                             2061

<210> SEQ ID NO 4
<211> LENGTH: 2061
<212> TYPE: RNA
<213> ORGANISM: Artificial Sequence
<220> FEATURE:
<223> OTHER INFORMATION: Synthetic Polynucleotide

<400> SEQUENCE: 4 augggcugg ugagccuggc caucgugacc gccugcgccg cgccgugga ggugaccaga       60 agaggcagcg ccuacuacau guaccuggac agaagcgacg ccggcgaggc caucagcuuc    120
ccuaccaccc ugggcaugaa caagugcuac auccagauca uggaccuggg ccacaugugc    180
gacgccacca ugagcuacga gugcccuaug cuggacgagg cguggagcc ugacgacgug     240 gacugcuggu gcaacaccac cagcaccugg guggugacg gcaccugcca ccacaagaag    300
ggcgaggcca agaagcag aagagccgug acccugccua gccacagcac cagaaagcug      360
cagaccagaa gccagaccug gcuggagagc agagaguaca ccaagcaccu gaucagagug    420
gagaacugga ucuucagaaa cccuggcuuc gcccuggccg ccgccgccau cgccuggcug    480
cugggcagca gcaccagcca gaaggugauc uaccugguga ugauccugcu gaucgccccu    540
gccuacagca ucagaugcau cggcgugagc aacagagacu cguggaggg caugagcggc    600 ggcaccuggg uggacguggu gcuggagcac ggcggcugcg ugaccgugau ggcccaggac    660
aagccugccg uggacaucga gcuggugacc accaccguga gcaacauggc cgaggugaga   720
agcuacugcu acgaggccag caucagcgac auggccagcg acagcagaug cccuagagag   780
ggcgaggccu accuggacaa gcagagcgac acccaguacg ugcaagag aacccuggug     840 gacagaggca gaggcaacgg cugcggcaga uucggcaagg gcagccuggu gaccugcgcc    900
aaguucgccu gcagcaagaa gaugaccggc aagagcaucc agccugagaa ccuggaguac   960
agaaucaugc ugagcgugca cggcagccag cacagcggca ugaucgugaa cgacaccggc   1020
cacgagaccg acgagaacag agccaaggug gagaucaccc cuaacagccc uagagccgag   1080
```

```
gccacccugg gcggcuucgg cagccugggc cuggacugcg agccuagaac cggccuggac    1140
uucagcgacc uguacuaccu gaccaugaac aacaagcacu ggcuggugca caaggagugg    1200
uuccacgaca ucccucugcc uuggcacgcc ggcgccgaca ccggcacccc ucacuggaac    1260
aacaaggagg cccuggugga guucaaggac gcccacgcca agagacagac cguggugug     1320 cugggcagcc aggagggcgc cgugcacacc gcccuggccg cgcccuggga ggccgagaug    1380
gacggcgcca agggcagacu gagcagcggc caccugaagu gcagacugaa gauggacaag    1440
cugagacuga agggcgugag cuacagccug ugcaccgccg ccuucaccuu caccaagauc    1500
ccugccgaga cccugcacgg caccgugacc guggaggugc aguacgccgg caccgacggc    1560
ccuugcaagg ugccugccca gauggccgug gacaugcaga cccugacccc ugugggcaga    1620
cugaucaccg ccaacccugu gaucaccgag agcaccgaga acagcaagau gaugcuggag    1680 cuggaccccuc cuuucggcga cagcuacauc gugaucggcg uggcgagaa aagaucacc     1740 caccacuggc acagaagcgg cagcaccauc ggcaaggccu ucgaggccac cgugagaggc    1800
gccaagagaa uggccgugcu gggcgacacc gccugggacu cggcagcgu gggcggcgcc     1860 cugaacagcc ugggcaaggg cauccaccag aucuucggcg ccgccuucaa gagccuguuc    1920
ggcggcauga gcugguucag ccagauccug aucggcaccc ugcuggugug cugggccug     1980 aacaccaaga acggcagcau cagccugacc ugccuggccc ugggcggcgu gcugaucuuc    2040
cugagcaccg ccgugagcgc c                                              2061

<210> SEQ ID NO 5
<211> LENGTH: 2049
<212> TYPE: RNA
<213> ORGANISM: Artificial Sequence
<220> FEATURE:
<223> OTHER INFORMATION: Synthetic Polynucleotide

<400> SEQUENCE: 5
auguggcugg ugagccuggc caucgugaca gcgugcgcug agccgccga gaucaccaga       60 agaggcagcg ccuacuacau guaccuggac agaagcgacg ccggcaaggc caucagcuuc     120
gccaccaccc ugggcgugaa caagugccac gugcagauca uggaccuggg ccacaugugc     180
gacgccacca ugagcuacga gugcccuaug cuggacgagg gcguggagcc ugacgacgug     240
gacugcuggu gcaacaccac cagcaccugg gugguguacg gcaccugcca ccacaagaag     300
ggcgaggcca agaagcag acgugccgug acccugccua ccacagcac cagaaagcug       360 cagaccagaa gccagaccug gcuggagagc agagaguaca ccaagcaccu gaucaaggug     420
gagaacugga ucuucagaaa cccuggcuuc gccuggugg ccgugggaau gccuggcug       480 cugggcagcu ccacaagcca gaaggugauc uaccuggug aucaccugcu gaucgcucca    540
gccuacagca uccgaugcau cggcgugagc aacagagacu cguggaggg caugagcggc    600 ggaaccuggg uugacguggu gcuggagcac ggcggcugcg ugaccgugau ggcccaggac    660
aagccuaccg uggacaucga gcuggugacc accaccgua gcaauggc cgaggugaga     720 agcuacugcu acgaggcauc caucagcgac auggccagcg acagccgcug cccuaccag    780 ggcgaagcau accucgauaa gcagagcgac acccaguaccg ugcaagag aacucucgug     840 gacagaggcu ggcaacgg cugcggccug uucggcaagg gcagccuggu ucuugcgcc     900 aguucaccu gcagcaagaa gaugaccggc aagagcaucc agccugagaa ccuggaguac    960
agaaucaugc ugagcgugca ggcagccag cacagcggca ugaucggcua cgaaacgac    1020 gaggacagag ccaaggucga agugaccccu aacagcccua gagccgaggc caccccuugga    1080
```

| | | |
|---|---|---|
| ggcuucggcu cccucggccu ggacugcgag ccuagaacag gacucgacuu cagcgaccug | 1140 | |
| uacuaccuga ccaugaacaa caagcacugg cugguccaca aggagugguu ccacgacauc | 1200 | |
| ccucugccuu ggcacgccgg agcagacacc ggcacccuc acuggaauaa caaggaggcg | 1260 | |
| cuuguggagu ucaaggacgc ccacgccaag agacagaccg gguugugcu cggaagucag | 1320 | |
| gagggcgccg ugcacaccgc ccuggccgga gcccuggagg ccgagaugga cggcgcaaag | 1380 | |
| ggcagacugu ucagcggcca ccugaagugc agacugaaga uggacaagcu gagacuuaag | 1440 | |
| ggcgucagcu acagccugug caccgccgcc uucaccuuca ccaaggugcc ugccgaaacc | 1500 | |
| cugcacggaa cuguaaccgu agagguccag uacgcaggaa ccgacggccc uugcaagauc | 1560 | |
| ccugugcaga ugggcggguga uaugcagacc cugacccug uuggccguuu gaucaccgcc | 1620 | |
| aacccuguga uaaccgagag caccgagaac agcaagauga ugcuggaacu ggacccuccu | 1680 | |
| uucggcgaca gcuacaucgu gaucggagug ggcgauaaga agaucaccca ccacuggcau | 1740 | |
| cgcagcgguu cuaccaucgg aaaggccuuc gaagcuaccg uuagagguga aaagcgcaug | 1800 | |
| gcagucuuag ugacaccgc cugggacuuc gguucugucg gaggcguguu caacagucug | 1860 | |
| ggcaagggaa uccaccagau cuucggcgcu gccuucaagu cuuguuucgg agguaugucu | 1920 | |
| ugguucagcc agauccugau cggcacccuu cugguuggc ugggccucaa caccaagaac | 1980 | |
| ggauccauau cccugaccug ccuggccuug ggcguguca ugaucuuccu gucgacugcc | 2040 | |
| gugagcgcc | 2049 | |

<210> SEQ ID NO 6
<211> LENGTH: 2049
<212> TYPE: RNA
<213> ORGANISM: Artificial Sequence
<220> FEATURE:
<223> OTHER INFORMATION: Synthetic Polynucleotide

<400> SEQUENCE: 6

| | | |
|---|---|---|
| auguggcugg ugagccuggc caucgugacu gcuugcgcgg gugccgccga gaucaccaga | 60 | |
| agaggcagcg ccuacuacau guaccuggac agaagcgacg ccggcaaggc caucagcuuc | 120 | |
| gccaccaccc ugggcgugaa caagugccac gugcagauca uggaccuggg ccacaugugc | 180 | |
| gacgccacca ugagcuacga gugcccuaug cuggacgagg gcguggagcc ugacgacgug | 240 | |
| gacugcuggu gcaacaccac cagcaccugg guguguacgc gcaccugcca ccacaagaag | 300 | |
| ggcgaggcca aagaagcag gagggccgug acccugccua gccacagcac cagaaagcug | 360 | |
| cagaccagaa gccagaccug gcuggagagc agagaguaca ccaagcaccu gaucaaggug | 420 | |
| gagaacugga ucuucagaaa cccuggcuuc gcccugguug gccguggcuau agccuggcug | 480 | |
| cugggaucuu caacaagcca gaaggugauc uaccuggua ugauccugcu gaucgcgcca | 540 | |
| gccuacagca uccgcugcau cggcgugagc aacagagacu ucguggaggg caugagcggc | 600 | |
| ggaacuuggg uggacguggu gcuggagcac ggcggcugcg ugaccgugau ggcccaggac | 660 | |
| aagccuaccg uggacaucga gcuggugacc accacgguuu cuaauauggc cgaggugaga | 720 | |
| agcuacugcu acgaggcauc caucagcgac auggccagcg acagcagggug ccuagagaa | 780 | |
| ggagaagccu aucucgacaa gcagagcgac acccaguacg ugugcaagag aacccucgug | 840 | |
| gacagaggca gaggcaacgg cugcggcaga uucggcaagg gcagccuggu acgugcgcc | 900 | |
| aaguucaccu gcagcaagaa gaugaccggc aagagcaucc agccugagaa ccuggaguac | 960 | |
| agaaucaugc ugagcgugca cggcagccag cacagcggca ugaucggcua cgagacagac | 1020 | |

```
gaggacagag cuaaggucga ggugacccou aacuccccac gcgccgaggc uacgcuggga    1080
ggcuucggau cucugggccu ggacugcgag ccuagaaccg gcuuggauuu cagcgaccug    1140
uacuaccuga ccaugaacaa caagcacugg uugguccaca aggagugguu ccacgacauc    1200
ccucugccuu ggcacgcggg cgcugacacc ggcacccouc acuggaauaa caaggaggcc    1260 uuggugagu caaggacgc ccacgccaag agacagaccg ugguggucuu ggguucccag      1320
gagggcgccg ugcacaccgc ccuggcagga gcucuggagg ccgagaugga cggcgccaag    1380
gguagacugu ucagcggcca ccugaagugc agacugaaga uggauaagcu gagacucaag    1440
ggugugucau acagccugug caccgccgcc uucaccuuca ccaaggugcc ugccgaaacc    1500
cugcacggaa ccgugacugu agagguacag uacgcuggca ccgacggccc uugcaagauc    1560
ccugugcaga uggccguuga caugcagacc cugaccccug ugggcaggcu gaucaccgcc    1620
aacccuguga ucacugagag caccgagaac agcaagauga ugcuggaacu ggacccuccu    1680
uucggcgaca gcuacaucgu gauaggcgug ggcgauaaga agaucaccca ccauuggcac    1740 agaaguggu cgacuaucgg uaaggcauuc gaagcuacag ugagggagc caagaggaug      1800 gcagugcugg ugacaccgc cugggauuuc gguucagugg gcggcguguu caauucccug     1860
ggcaagggua uccaccagau cuucggcgcu gccuucaaga gccuguucgg uggaaugagc    1920
ugguucagcc agauccugau cggcaccccuc cugguuuggc uugguuugaa caccaagaac   1980
ggcucuauuu cccugaccug ccuggcacua ggaggcguca ugauauuccu gaguaccgcc    2040
gugagcgcc                                                           2049
```

<210> SEQ ID NO 7
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 7

```
Met Trp Leu Val Ser Leu Ala Ile Val Thr Ala Cys Ala Gly Ala Ala
1               5                   10                  15

Glu Val Thr Arg Arg Gly Ser Ala Tyr Tyr Met Tyr Leu Asp Arg Asn
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
    130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175
```

```
Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
            195                 200                 205

Glu His Gly Gly Cys Val Thr Val Met Ala Gln Asp Lys Pro Thr Val
            210                 215                 220

Asp Ile Glu Leu Val Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                    245                 250                 255

Cys Pro Thr Gln Gly Glu Ala Tyr Leu Asp Lys Gln Ser Asp Thr Gln
            260                 265                 270

Tyr Val Cys Lys Arg Thr Leu Val Asp Arg Gly Trp Gly Asn Gly Cys
            275                 280                 285

Gly Leu Phe Gly Lys Gly Ser Leu Val Thr Cys Ala Lys Phe Ala Cys
            290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                    325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
            355                 360                 365

Leu Gly Leu Asp Cys Glu Pro Arg Thr Gly Leu Asp Phe Ser Asp Leu
370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                    405                 410                 415

Pro His Trp Asn Asn Lys Glu Ala Leu Val Glu Phe Lys Asp Ala His
            420                 425                 430

Ala Lys Arg Gln Thr Val Val Val Leu Gly Ser Gln Glu Gly Ala Val
            435                 440                 445

His Thr Ala Leu Ala Gly Ala Leu Glu Ala Glu Met Asp Gly Ala Lys
450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                    485                 490                 495

Phe Thr Lys Ile Pro Ala Glu Thr Leu His Gly Thr Val Thr Val Glu
            500                 505                 510

Val Gln Tyr Ala Gly Thr Asp Gly Pro Cys Lys Val Pro Ala Gln Met
            515                 520                 525

Ala Val Asp Met Gln Thr Leu Thr Pro Val Gly Arg Leu Ile Thr Ala
530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                    565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
```

```
                595                 600                 605
Asp Thr Ala Trp Asp Phe Gly Ser Val Gly Gly Ala Leu Asn Ser Leu
            610                 615                 620
Gly Lys Gly Ile His Gln Ile Phe Gly Ala Ala Phe Lys Ser Leu Phe
625                 630                 635                 640
Gly Gly Met Ser Trp Phe Ser Gln Ile Leu Ile Gly Thr Leu Leu Met
                645                 650                 655
Trp Leu Gly Leu Asn Thr Lys Asn Gly Ser Ile Ser Leu Met Cys Leu
            660                 665                 670
Ala Leu Gly Gly Val Leu Ile Phe Leu Ser Thr Ala Val Ser Ala
            675                 680                 685

<210> SEQ ID NO 8
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 8

Met Trp Leu Val Ser Leu Ala Ile Val Thr Ala Cys Ala Gly Ala Ala
1               5                   10                  15
Glu Val Thr Arg Arg Gly Ser Ala Tyr Tyr Met Tyr Leu Asp Arg Asn
            20                  25                  30
Asp Ala Gly Glu Ala Ile Ser Phe Pro Thr Thr Leu Gly Met Asn Lys
        35                  40                  45
Cys Tyr Ile Gln Ile Met Asp Leu Gly His Met Cys Asp Ala Thr Met
    50                  55                  60
Ser Tyr Glu Cys Pro Met Leu Asp Glu Gly Val Glu Pro Asp Asp Val
65                  70                  75                  80
Asp Cys Trp Cys Asn Thr Thr Ser Thr Trp Val Val Tyr Gly Thr Cys
                85                  90                  95
His His Lys Lys Gly Glu Ala Arg Arg Ser Arg Arg Ala Val Thr Leu
            100                 105                 110
Pro Ser His Ser Thr Arg Lys Leu Gln Thr Arg Ser Gln Thr Trp Leu
        115                 120                 125
Glu Ser Arg Glu Tyr Thr Lys His Leu Ile Arg Val Glu Asn Trp Ile
    130                 135                 140
Phe Arg Asn Pro Gly Phe Ala Leu Ala Ala Ala Ile Ala Trp Leu
145                 150                 155                 160
Leu Gly Ser Ser Thr Ser Gln Lys Val Ile Tyr Leu Val Met Ile Leu
                165                 170                 175
Leu Ile Ala Pro Ala Tyr Ser Ile Arg Cys Ile Gly Val Ser Asn Arg
            180                 185                 190
Asp Phe Val Glu Gly Met Ser Gly Gly Thr Trp Val Asp Val Val Leu
        195                 200                 205
Glu His Gly Gly Cys Val Thr Val Met Ala Gln Asp Lys Pro Thr Val
    210                 215                 220
Asp Ile Glu Leu Val Thr Thr Thr Val Ser Asn Met Ala Glu Val Arg
225                 230                 235                 240
Ser Tyr Cys Tyr Glu Ala Ser Ile Ser Asp Met Ala Ser Asp Ser Arg
                245                 250                 255
Cys Pro Arg Glu Gly Glu Ala Tyr Leu Asp Lys Gln Ser Asp Thr Gln
            260                 265                 270
Tyr Val Cys Lys Arg Thr Leu Val Asp Arg Gly Arg Gly Asn Gly Cys
```

275                 280                 285
Gly Arg Phe Gly Lys Gly Ser Leu Val Thr Cys Ala Lys Phe Ala Cys
290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
355                 360                 365

Leu Gly Leu Asp Cys Glu Pro Arg Thr Gly Leu Asp Phe Ser Asp Leu
370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                405                 410                 415

Pro His Trp Asn Asn Lys Glu Ala Leu Val Glu Phe Lys Asp Ala His
            420                 425                 430

Ala Lys Arg Gln Thr Val Val Leu Gly Ser Gln Glu Gly Ala Val
        435                 440                 445

His Thr Ala Leu Ala Gly Ala Leu Glu Ala Glu Met Asp Gly Ala Lys
450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
            500                 505                 510

Val Gln Tyr Ala Gly Thr Asp Gly Pro Cys Lys Val Pro Ala Gln Met
        515                 520                 525

Ala Val Asp Met Gln Thr Leu Thr Pro Val Gly Arg Leu Ile Thr Ala
530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
        595                 600                 605

Asp Thr Ala Trp Asp Phe Gly Ser Val Gly Gly Ala Leu Asn Ser Leu
610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Met
                645                 650                 655

Trp Leu Gly Leu Asn Thr Lys Asn Gly Ser Ile Ser Leu Met Cys Leu
            660                 665                 670

Ala Leu Gly Gly Val Leu Ile Phe Leu Ser Thr Ala Val Ser Ala
        675                 680                 685

<210> SEQ ID NO 9

<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 9

```
Met Trp Leu Val Ser Leu Ala Ile Val Thr Ala Cys Ala Gly Ala Val
1               5                   10                  15

Glu Val Thr Arg Arg Gly Ser Ala Tyr Tyr Met Tyr Leu Asp Arg Ser
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
    130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Ala Val
    210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Thr Gln Gly Glu Ala Tyr Leu Asp Lys Gln Ser Asp Thr Gln
            260                 265                 270

Tyr Val Cys Lys Arg Thr Leu Val Asp Arg Gly Trp Gly Asn Gly Cys
        275                 280                 285

Gly Leu Phe Gly Lys Gly Ser Leu Val Thr Cys Ala Lys Phe Ala Cys
    290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
        355                 360                 365

Leu Gly Leu Asp Cys Glu Pro Arg Thr Gly Leu Asp Phe Ser Asp Leu
    370                 375                 380
```

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
            405                 410                 415

Pro His Trp Asn Asn Lys Glu Ala Leu Val Glu Phe Lys Asp Ala His
        420                 425                 430

Ala Lys Arg Gln Thr Val Val Leu Gly Ser Gln Glu Gly Ala Val
    435                 440                 445

His Thr Ala Leu Ala Gly Ala Leu Glu Ala Glu Met Asp Gly Ala Lys
450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
            500                 505                 510

Val Gln Tyr Ala Gly Thr Asp Gly Pro Cys Lys Val Pro Ala Gln Met
        515                 520                 525

Ala Val Asp Met Gln Thr Leu Thr Pro Val Gly Arg Leu Ile Thr Ala
530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
        595                 600                 605

Asp Thr Ala Trp Asp Phe Gly Ser Val Gly Gly Ala Leu Asn Ser Leu
610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Val
                645                 650                 655

Trp Leu Gly Leu Asn Thr Lys Asn Gly Ser Ile Ser Leu Thr Cys Leu
            660                 665                 670

Ala Leu Gly Gly Val Leu Ile Phe Leu Ser Thr Ala Val Ser Ala
        675                 680                 685

<210> SEQ ID NO 10
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 10

Met Trp Leu Val Ser Leu Ala Ile Val Thr Ala Cys Ala Gly Ala Val
1               5                   10                  15

Glu Val Thr Arg Arg Gly Ser Ala Tyr Tyr Met Tyr Leu Asp Arg Ser
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60

-continued

Ser Tyr Glu Cys Pro Met Leu Asp Glu Gly Val Glu Pro Asp Asp Val
 65                  70                  75                  80

Asp Cys Trp Cys Asn Thr Thr Ser Thr Trp Val Val Tyr Gly Thr Cys
                 85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
            115                 120                 125

Glu Ser Arg Glu Tyr Thr Lys His Leu Ile Arg Val Glu Asn Trp Ile
            130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
                180                 185                 190

Asp Phe Val Glu Gly Met Ser Gly Gly Thr Trp Val Asp Val Val Leu
            195                 200                 205

Glu His Gly Gly Cys Val Thr Val Met Ala Gln Asp Lys Pro Ala Val
210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Arg Glu Gly Glu Ala Tyr Leu Asp Lys Gln Ser Asp Thr Gln
            260                 265                 270

Tyr Val Cys Lys Arg Thr Leu Val Asp Arg Gly Arg Gly Asn Gly Cys
            275                 280                 285

Gly Arg Phe Gly Lys Gly Ser Leu Val Thr Cys Ala Lys Phe Ala Cys
290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
            355                 360                 365

Leu Gly Leu Asp Cys Glu Pro Arg Thr Gly Leu Asp Phe Ser Asp Leu
            370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                405                 410                 415

Pro His Trp Asn Asn Lys Glu Ala Leu Val Glu Phe Lys Asp Ala His
            420                 425                 430

Ala Lys Arg Gln Thr Val Val Val Leu Gly Ser Gln Glu Gly Ala Val
            435                 440                 445

His Thr Ala Leu Ala Gly Ala Leu Glu Ala Glu Met Asp Gly Ala Lys
            450                 455                 460

Gly Arg Leu Ser Ser Gly His Leu Lys Cys Arg Leu Lys Met Asp Lys
465                 470                 475                 480

-continued

```
Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
            500                 505                 510

Val Gln Tyr Ala Gly Thr Asp Gly Pro Cys Lys Val Pro Ala Gln Met
        515                 520                 525

Ala Val Asp Met Gln Thr Leu Thr Pro Val Gly Arg Leu Ile Thr Ala
    530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
        595                 600                 605

Asp Thr Ala Trp Asp Phe Gly Ser Val Gly Gly Ala Leu Asn Ser Leu
    610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Val
                645                 650                 655

Trp Leu Gly Leu Asn Thr Lys Asn Gly Ser Ile Ser Leu Thr Cys Leu
            660                 665                 670

Ala Leu Gly Gly Val Leu Ile Phe Leu Ser Thr Ala Val Ser Ala
        675                 680                 685

<210> SEQ ID NO 11
<211> LENGTH: 683
<212> TYPE: PRT
<213> ORGANISM: Artificial Sequence
<220> FEATURE:
<223> OTHER INFORMATION: Synthetic Polypeptide

<400> SEQUENCE: 11

Met Trp Leu Val Ser Leu Ala Ile Val Thr Ala Cys Ala Gly Ala Ala
1               5                   10                  15

Glu Ile Thr Arg Arg Gly Ser Ala Tyr Tyr Met Tyr Leu Asp Arg Ser
            20                  25                  30

Asp Ala Gly Lys Ala Ile Ser Phe Ala Thr Thr Leu Gly Val Asn Lys
        35                  40                  45

Cys His Val Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Lys Val Glu Asn Trp Ile
    130                 135                 140

Phe Arg Asn Pro Gly Phe Ala Leu Val Ala Val Ala Ile Ala Trp Leu
145                 150                 155                 160
```

-continued

```
Leu Gly Ser Ser Thr Ser Gln Lys Val Ile Tyr Leu Val Met Ile Leu
            165                 170                 175
Leu Ile Ala Pro Ala Tyr Ser Ile Arg Cys Ile Gly Val Ser Asn Arg
        180                 185                 190
Asp Phe Val Glu Gly Met Ser Gly Thr Trp Val Asp Val Val Leu
    195                 200                 205
Glu His Gly Gly Cys Val Thr Val Met Ala Gln Asp Lys Pro Thr Val
    210                 215                 220
Asp Ile Glu Leu Val Thr Thr Thr Val Ser Asn Met Ala Glu Val Arg
225                 230                 235                 240
Ser Tyr Cys Tyr Glu Ala Ser Ile Ser Asp Met Ala Ser Asp Ser Arg
            245                 250                 255
Cys Pro Thr Gln Gly Glu Ala Tyr Leu Asp Lys Gln Ser Asp Thr Gln
        260                 265                 270
Tyr Val Cys Lys Arg Thr Leu Val Asp Arg Gly Trp Gly Asn Gly Cys
    275                 280                 285
Gly Leu Phe Gly Lys Gly Ser Leu Val Thr Cys Ala Lys Phe Thr Cys
        290                 295                 300
Ser Lys Lys Met Thr Gly Lys Ser Ile Gln Pro Glu Asn Leu Glu Tyr
305                 310                 315                 320
Arg Ile Met Leu Ser Val His Gly Ser Gln His Ser Gly Met Ile Gly
            325                 330                 335
Tyr Glu Thr Asp Glu Asp Arg Ala Lys Val Glu Val Thr Pro Asn Ser
        340                 345                 350
Pro Arg Ala Glu Ala Thr Leu Gly Gly Phe Gly Ser Leu Gly Leu Asp
    355                 360                 365
Cys Glu Pro Arg Thr Gly Leu Asp Phe Ser Asp Leu Tyr Tyr Leu Thr
370                 375                 380
Met Asn Asn Lys His Trp Leu Val His Lys Glu Trp Phe His Asp Ile
385                 390                 395                 400
Pro Leu Pro Trp His Ala Gly Ala Asp Thr Gly Thr Pro His Trp Asn
            405                 410                 415
Asn Lys Glu Ala Leu Val Glu Phe Lys Asp Ala His Ala Lys Arg Gln
        420                 425                 430
Thr Val Val Leu Gly Ser Gln Glu Gly Ala Val His Thr Ala Leu
    435                 440                 445
Ala Gly Ala Leu Glu Ala Glu Met Asp Gly Ala Lys Gly Arg Leu Phe
    450                 455                 460
Ser Gly His Leu Lys Cys Arg Leu Lys Met Asp Lys Leu Arg Leu Lys
465                 470                 475                 480
Gly Val Ser Tyr Ser Leu Cys Thr Ala Ala Phe Thr Phe Thr Lys Val
            485                 490                 495
Pro Ala Glu Thr Leu His Gly Thr Val Thr Val Glu Val Gln Tyr Ala
        500                 505                 510
Gly Thr Asp Gly Pro Cys Lys Ile Pro Val Gln Met Ala Val Asp Met
    515                 520                 525
Gln Thr Leu Thr Pro Val Gly Arg Leu Ile Thr Ala Asn Pro Val Ile
    530                 535                 540
Thr Glu Ser Thr Glu Asn Ser Lys Met Met Leu Glu Leu Asp Pro Pro
545                 550                 555                 560
Phe Gly Asp Ser Tyr Ile Val Ile Gly Val Gly Asp Lys Lys Ile Thr
            565                 570                 575
His His Trp His Arg Ser Gly Ser Thr Ile Gly Lys Ala Phe Glu Ala
```

```
                    580                 585                 590
Thr Val Arg Gly Ala Lys Arg Met Ala Val Leu Gly Asp Thr Ala Trp
            595                 600                 605

Asp Phe Gly Ser Val Gly Val Phe Asn Ser Leu Gly Lys Gly Ile
        610                 615                 620

His Gln Ile Phe Gly Ala Ala Phe Lys Ser Leu Phe Gly Gly Met Ser
625                 630                 635                 640

Trp Phe Ser Gln Ile Leu Ile Gly Thr Leu Leu Val Trp Leu Gly Leu
                645                 650                 655

Asn Thr Lys Asn Gly Ser Ile Ser Leu Thr Cys Leu Ala Leu Gly Gly
            660                 665                 670

Val Met Ile Phe Leu Ser Thr Ala Val Ser Ala
        675                 680

<210> SEQ ID NO 12
<211> LENGTH: 683
<212> TYPE: PRT
<213> ORGANISM: Artificial Sequence
<220> FEATURE:
<223> OTHER INFORMATION: Synthetic Polypeptide

<400> SEQUENCE: 12

Met Trp Leu Val Ser Leu Ala Ile Val Thr Ala Cys Ala Gly Ala Ala
1               5                   10                  15

Glu Ile Thr Arg Arg Gly Ser Ala Tyr Tyr Met Tyr Leu Asp Arg Ser
            20                  25                  30

Asp Ala Gly Lys Ala Ile Ser Phe Ala Thr Thr Leu Gly Val Asn Lys
        35                  40                  45

Cys His Val Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Lys Val Glu Asn Trp Ile
    130                 135                 140

Phe Arg Asn Pro Gly Phe Ala Leu Val Ala Val Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Thr Val
    210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Arg Glu Gly Glu Ala Tyr Leu Asp Lys Gln Ser Asp Thr Gln
```

-continued

```
                260                 265                 270
Tyr Val Cys Lys Arg Thr Leu Val Asp Arg Gly Arg Gly Asn Gly Cys
                275                 280                 285

Gly Arg Phe Gly Lys Gly Ser Leu Val Thr Cys Ala Lys Phe Thr Cys
            290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Gly
                325                 330                 335

Tyr Glu Thr Asp Glu Asp Arg Ala Lys Val Glu Val Thr Pro Asn Ser
            340                 345                 350

Pro Arg Ala Glu Ala Thr Leu Gly Gly Phe Gly Ser Leu Gly Leu Asp
        355                 360                 365

Cys Glu Pro Arg Thr Gly Leu Asp Phe Ser Asp Leu Tyr Tyr Leu Thr
    370                 375                 380

Met Asn Asn Lys His Trp Leu Val His Lys Glu Trp Phe His Asp Ile
385                 390                 395                 400

Pro Leu Pro Trp His Ala Gly Ala Asp Thr Gly Thr Pro His Trp Asn
                405                 410                 415

Asn Lys Glu Ala Leu Val Glu Phe Lys Asp Ala His Ala Lys Arg Gln
            420                 425                 430

Thr Val Val Leu Gly Ser Gln Glu Gly Ala Val His Thr Ala Leu
        435                 440                 445

Ala Gly Ala Leu Glu Ala Glu Met Asp Gly Ala Lys Gly Arg Leu Phe
    450                 455                 460

Ser Gly His Leu Lys Cys Arg Leu Lys Met Asp Lys Leu Arg Leu Lys
465                 470                 475                 480

Gly Val Ser Tyr Ser Leu Cys Thr Ala Ala Phe Thr Phe Thr Lys Val
                485                 490                 495

Pro Ala Glu Thr Leu His Gly Thr Val Thr Val Glu Val Gln Tyr Ala
            500                 505                 510

Gly Thr Asp Gly Pro Cys Lys Ile Pro Val Gln Met Ala Val Asp Met
        515                 520                 525

Gln Thr Leu Thr Pro Val Gly Arg Leu Ile Thr Ala Asn Pro Val Ile
    530                 535                 540

Thr Glu Ser Thr Glu Asn Ser Lys Met Met Leu Glu Leu Asp Pro Pro
545                 550                 555                 560

Phe Gly Asp Ser Tyr Ile Val Ile Gly Val Gly Asp Lys Lys Ile Thr
                565                 570                 575

His His Trp His Arg Ser Gly Ser Thr Ile Gly Lys Ala Phe Glu Ala
            580                 585                 590

Thr Val Arg Gly Ala Lys Arg Met Ala Val Leu Gly Asp Thr Ala Trp
        595                 600                 605

Asp Phe Gly Ser Val Gly Gly Val Phe Asn Ser Leu Gly Lys Gly Ile
    610                 615                 620

His Gln Ile Phe Gly Ala Ala Phe Lys Ser Leu Phe Gly Gly Met Ser
625                 630                 635                 640

Trp Phe Ser Gln Ile Leu Ile Gly Thr Leu Leu Val Trp Leu Gly Leu
                645                 650                 655

Asn Thr Lys Asn Gly Ser Ile Ser Leu Thr Cys Leu Ala Leu Gly Gly
            660                 665                 670

Val Met Ile Phe Leu Ser Thr Ala Val Ser Ala
        675                 680
```

<210> SEQ ID NO 13
<211> LENGTH: 57
<212> TYPE: RNA
<213> ORGANISM: Artificial Sequence
<220> FEATURE:
<223> OTHER INFORMATION: Synthetic Polynucleotide

<400> SEQUENCE: 13 gggaauaag agagaaaaga agaguaagaa gaaauauaag accccggcgc cgccacc         57

<210> SEQ ID NO 14
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 14 gggaauaag agagaaaaga agaguaagaa gaaauauaag agccacc                   47

<210> SEQ ID NO 15
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 15
ugauaauagg cuggagccuc gguggccuag cuucuugccc cuugggccuc ccccagccc      60 cuccuccccu uccugcaccc guaccccgu ggucuuugaa uaaagucuga gugggcggc      119

<210> SEQ ID NO 16
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 16
ugauaauagg cuggagccuc gguggccaug cuucuugccc cuugggccuc ccccagccc      60 cuccuccccu uccugcaccc guaccccgu ggucuuugaa uaaagucuga gugggcggc      119

<210> SEQ ID NO 17
<211> LENGTH: 690
<212> TYPE: PRT
<213> ORGANISM: Artificial Sequence
<220> FEATURE:
<223> OTHER INFORMATION: Synthetic Polypeptide

<400> SEQUENCE: 17

Met Asp Trp Thr Trp Ile Leu Phe Leu Val Ala Ala Thr Arg Val
1               5                   10                  15

His Ser Val Glu Val Thr Arg Arg Gly Ser Ala Tyr Tyr Met Tyr Leu
            20                  25                  30

Asp Arg Ser Asp Ala Gly Glu Ala Ile Ser Phe Pro Thr Thr Leu Gly
        35                  40                  45

Met Asn Lys Cys Tyr Ile Gln Ile Met Asp Leu Gly His Met Cys Asp
    50                  55                  60

Ala Thr Met Ser Tyr Glu Cys Pro Met Leu Asp Glu Gly Val Glu Pro
65                  70                  75                  80

Asp Asp Val Asp Cys Trp Cys Asn Thr Thr Ser Thr Trp Val Val Tyr

```
                    85                  90                  95
Gly Thr Cys His His Lys Lys Gly Glu Ala Arg Arg Ser Arg Arg Ala
                100                 105                 110

Val Thr Leu Pro Ser His Ser Thr Arg Lys Leu Gln Thr Arg Ser Gln
            115                 120                 125

Thr Trp Leu Glu Ser Arg Glu Tyr Thr Lys His Leu Ile Arg Val Glu
        130                 135                 140

Asn Trp Ile Phe Arg Asn Pro Gly Phe Ala Leu Ala Ala Ala Ala Ile
145                 150                 155                 160

Ala Trp Leu Leu Gly Ser Ser Thr Ser Gln Lys Val Ile Tyr Leu Val
                165                 170                 175

Met Ile Leu Leu Ile Ala Pro Ala Tyr Ser Ile Arg Cys Ile Gly Val
                180                 185                 190

Ser Asn Arg Asp Phe Val Glu Gly Met Ser Gly Gly Thr Trp Val Asp
            195                 200                 205

Val Val Leu Glu His Gly Gly Cys Val Thr Val Met Ala Gln Asp Lys
        210                 215                 220

Pro Ala Val Asp Ile Glu Leu Val Thr Thr Thr Val Ser Asn Met Ala
225                 230                 235                 240

Glu Val Arg Ser Tyr Cys Tyr Glu Ala Ser Ile Ser Asp Met Ala Ser
                245                 250                 255

Asp Ser Arg Cys Pro Thr Gln Gly Glu Ala Tyr Leu Asp Lys Gln Ser
            260                 265                 270

Asp Thr Gln Tyr Val Cys Lys Arg Thr Leu Val Asp Arg Gly Trp Gly
        275                 280                 285

Asn Gly Cys Gly Leu Phe Gly Lys Gly Ser Leu Val Thr Cys Ala Lys
290                 295                 300

Phe Ala Cys Ser Lys Lys Met Thr Gly Lys Ser Ile Gln Pro Glu Asn
305                 310                 315                 320

Leu Glu Tyr Arg Ile Met Leu Ser Val His Gly Ser Gln His Ser Gly
                325                 330                 335

Met Ile Val Asn Asp Thr Gly His Glu Thr Asp Glu Asn Arg Ala Lys
            340                 345                 350

Val Glu Ile Thr Pro Asn Ser Pro Arg Ala Glu Ala Thr Leu Gly Gly
        355                 360                 365

Phe Gly Ser Leu Gly Leu Asp Cys Glu Pro Arg Thr Gly Leu Asp Phe
    370                 375                 380

Ser Asp Leu Tyr Tyr Leu Thr Met Asn Asn Lys His Trp Leu Val His
385                 390                 395                 400

Lys Glu Trp Phe His Asp Ile Pro Leu Pro Trp His Ala Gly Ala Asp
                405                 410                 415

Thr Gly Thr Pro His Trp Asn Asn Lys Glu Ala Leu Val Glu Phe Lys
            420                 425                 430

Asp Ala His Ala Lys Arg Gln Thr Val Val Val Leu Gly Ser Gln Glu
        435                 440                 445

Gly Ala Val His Thr Ala Leu Ala Gly Ala Leu Glu Ala Glu Met Asp
    450                 455                 460

Gly Ala Lys Gly Arg Leu Ser Ser Gly His Leu Lys Cys Arg Leu Lys
465                 470                 475                 480

Met Asp Lys Leu Arg Leu Lys Gly Val Ser Tyr Ser Leu Cys Thr Ala
                485                 490                 495

Ala Phe Thr Phe Thr Lys Ile Pro Ala Glu Thr Leu His Gly Thr Val
            500                 505                 510
```

```
Thr Val Glu Val Gln Tyr Ala Gly Thr Asp Gly Pro Cys Lys Val Pro
        515                 520                 525

Ala Gln Met Ala Val Asp Met Gln Thr Leu Thr Pro Val Gly Arg Leu
    530                 535                 540

Ile Thr Ala Asn Pro Val Ile Thr Glu Ser Thr Glu Asn Ser Lys Met
545                 550                 555                 560

Met Leu Glu Leu Asp Pro Pro Phe Gly Asp Ser Tyr Ile Val Ile Gly
            565                 570                 575

Val Gly Glu Lys Lys Ile Thr His His Trp His Arg Ser Gly Ser Thr
        580                 585                 590

Ile Gly Lys Ala Phe Glu Ala Thr Val Arg Gly Ala Lys Arg Met Ala
    595                 600                 605

Val Leu Gly Asp Thr Ala Trp Asp Phe Gly Ser Val Gly Gly Ala Leu
    610                 615                 620

Asn Ser Leu Gly Lys Gly Ile His Gln Ile Phe Gly Ala Ala Phe Lys
625                 630                 635                 640

Ser Leu Phe Gly Gly Met Ser Trp Phe Ser Gln Ile Leu Ile Gly Thr
            645                 650                 655

Leu Leu Val Trp Leu Gly Leu Asn Thr Lys Asn Gly Ser Ile Ser Leu
        660                 665                 670

Thr Cys Leu Ala Leu Gly Gly Val Leu Ile Phe Leu Ser Thr Ala Val
    675                 680                 685

Ser Ala
    690

<210> SEQ ID NO 18
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 18

Met Trp Leu Val Ser Leu Ala Ile Val Thr Ala Cys Ala Gly Ala
1               5                   10                  15

<210> SEQ ID NO 19
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 19
auguggcugg ugucccuggc caucgugaca gccugugcug gcgcc                              45

<210> SEQ ID NO 20
<211> LENGTH: 2337
<212> TYPE: RNA
<213> ORGANISM: Artificial Sequence
<220> FEATURE:
<223> OTHER INFORMATION: Synthetic Polynucleotide

<400> SEQUENCE: 20
gggaaauaag agagaaaaga agaguaagaa gaaauauaag accccggcgc cgccaccaug      60
uggcuggugu cccuggccau cgugacagcc ugugcuggcg ccgcugaagu gaccagaaga     120
ggcagcgccu acuacaugua ccuggaccgg aacgaugccg cgaggccau cagcuuucca     180 accacccugg gcaugaacaa gugcuacauc cagaucaugg accuggcca caugugcgac     240
```

```
gccaccauga gcuacgagug ccccaugcug gacgagggcg uggaacccga cgauguggac      300
ugcuggugca acaccaccag caccugggug guguacggca ccugucacca caagaagggc      360
gaagccagac gguccagacg ggccgugaca cugccuagcc acagcaccag aaagcugcag      420
acccggnccc agaccuggcu ggaaagcaga gaguacacca agcaccugau ccggguggaa      480
aacuggaucu uccggaaccc cggcuuugcc cuggccgcug cugcuauugc uuggcugcug      540
ggcagcagca ccucccagaa agugaucuac cucgugauga uccugcugau cgccccugcc      600
uacagcaucc gguguaucgg cguguccaac cgggacuucg uggaaggcau gagcggcggc      660 acauggugg acguggugcu ggaacauggc ggcugcguga cagugauggc ccaggacaag      720
cccaccgugg acaucgagcu cgugaccacc accgugucca auauggccga agugcggagc      780
uacugcuacg aggccagcau cagcgacaug gccagcgaca gcagaugccc uacacagggc      840
gaggccuacc uggacaagca guccgacacc caguacgugu gcaagcggac ccugguggau      900
agaggcuggg gcaauggcug cggccuguuu ggcaagggca gccucgugac cugcgccaag      960
uucgccugca gcaagaagau gaccggcaag agcauccagc ccgagaaccu ggaauaccgg     1020
aucaugcuga gcgugcacgg cagccagcac uccggcauga ucgugaacga caccggccac     1080
gagacagacg agaaccgggc caagguggaa aucacccccua acagcccuag agccgaggcc     1140
acacugggcg gcuuuggauc ucugggccug gacugcgagc cuagaaccgg ccuggauuuc     1200
agcgaccugu acuaccugac caugaacaac aagcacuggc uggugcacaa agagugguuc     1260
cacgacaucc cucugcccug gcaugccggc gcugauacag gcacacccca cuggaacaac     1320
aaagaggcuc uggguggaauu caaggacgcc cacgccaagc ggcagaccgu ggugugcug     1380 ggaucucagg aaggcgccgu gcauacagcu cuggcaggcg cccuggaagc cgaaauggau     1440
ggcgccaaag gcagacuguc cagcggccac cugaagugcc ggcugaagau ggacaagcug     1500
cggcugaagg gcguguccua cucccugugu accgccgccu ucaccuucac caagauccccc    1560 gccgagacac ugcacggcac cgugacugug gaagugcagu acgccggcac cgacggcccu     1620
uguaaagugc cugcucagau ggccguggau augcagaccc ugacccccugu gggcagacug     1680 aucaccgcca accccgugau caccgagagc accgagaaca gcagaugau gcuggaacug      1740 gacccacccu ucggcgacag cuacaucgug aucggcgugg gagagaagaa gaucaccac      1800 cacuggcaca gaagcggcag caccaucggc aaggccuuug aggcuacagu gcggggagcc     1860
aagagaaugg ccgugcuggg agauaccgcc ugggacuuug gcucuguggg cggagcccug     1920
aacucucugg gcaagggaau ccaccagauc uucgagccgg ccuuuaagag ccuguucggc     1980
ggcaugagcu gguucagcca gauccugauc ggcacccugc ugaugugcu gggccugaac     2040 accaagaacg gcagcaucuc ccugaugugc cuggcucugg gaggcgugcu gaucuuccug    2100
agcacagccg ugucugccug auaauaggcu ggagccucgg uggccuagcu ucuugcccu     2160 ugggccuccc cccagcccu ccuccccuuc cugcacccgu accccgugg ucuuugaaua     2220 aagucugagu gggcggcaaa aaaaaaaaaa aaaaaaaaaa aaaaaaaaaa aaaaaaaaaa     2280
aaaaaaaaaa aaaaaaaaaa aaaaaaaaaa aaaaaaaaaa aaaaaaaaaa aaaaaaa       2337
```

UNITED STATES PATENT AND TRADEMARK OFFICE
CERTIFICATE OF CORRECTION

PATENT NO. : 10,653,767 B2
APPLICATION NO. : 16/131793
DATED : May 19, 2020
INVENTOR(S) : Giuseppe Ciaramella et al.

It is certified that error appears in the above-identified patent and that said Letters Patent is hereby corrected as shown below:

In the Specification

At Column 1, Line 10: insert the following paragraph:
--GOVERNMENT LICENSE RIGHTS
This invention was made with government support under Contract No. W911NF-13-1-0417 awarded by Defense Advanced Research Projects Agency (DARPA). The government has certain rights in the invention.--

Signed and Sealed this
Seventeenth Day of November, 2020

Andrei Iancu
*Director of the United States Patent and Trademark Office*